US012380564B2

United States Patent
Haley et al.

(10) Patent No.: US 12,380,564 B2
(45) Date of Patent: Aug. 5, 2025

(54) METHOD FOR REGISTERING TWO OR MORE PATIENT IMAGES FOR CHANGE ASSESSMENT OVER TIME

(71) Applicant: Veytel, Inc., Pittsburgh, PA (US)

(72) Inventors: Paul H. Haley, Easton, PA (US); Ellen K. Hughes, Pittsburgh, PA (US); Michael Hoffelder, Norwich, NY (US); Catherine M. Dietz, Redmond, WA (US); Kevin J. Mitchell, Altoona, PA (US)

(73) Assignee: Veytel, Inc., Pittsburgh, PA (US)

( * ) Notice: Subject to any disclaimer, the term of this patent is extended or adjusted under 35 U.S.C. 154(b) by 0 days.

(21) Appl. No.: 18/923,569

(22) Filed: Oct. 22, 2024

(65) Prior Publication Data

US 2025/0069229 A1 Feb. 27, 2025

Related U.S. Application Data

(63) Continuation of application No. PCT/US2023/019637, filed on Apr. 24, 2023.
(Continued)

(51) Int. Cl.
*G06K 9/00* (2022.01)
*G06T 7/00* (2017.01)

(52) U.S. Cl.
CPC ........ *G06T 7/0016* (2013.01); *G06T 2207/10* (2013.01); *G06T 2207/30088* (2013.01)

(58) Field of Classification Search
CPC .............................. G06T 7/0012–0016; G06T 2207/10064–10136;
(Continued)

(56) References Cited

U.S. PATENT DOCUMENTS 7,162,063 B1  1/2007 Craine et al.
8,045,263 B2 * 10/2011 Yaroslavsky ........ A61B 5/0071
359/368
(Continued)

OTHER PUBLICATIONS

K. Korotkov et al., "An Improved Skin Lesion Matching Scheme in Total Body Photography," in IEEE Journal of Biomedical and Health Informatics, vol. 23, No. 2, pp. 586-598, Mar. 2019 (Year: 2019).*
(Continued)

*Primary Examiner* — Atiba O Fitzpatrick
(74) *Attorney, Agent, or Firm* — Cody J. Madison; Eckert Seamans Cherin & Mellott LLC

(57) ABSTRACT

A system, method, and computer program product for registering two or more patient images for change assessment over time. An example aspect is configured to: obtain a new image of an area with an image capture system; obtain a reference image of a similar area; perform pre-processing of the new image and the reference image; perform a coarse alignment of the new image and the reference image; perform a high-resolution estimate; perform a high-resolution alignment; cross-check the at least one-point match to eliminate false matches and confirm correct matches of the high-resolution new image and the high-resolution reference image; perform segmentation of the high-resolution new image and the high-resolution reference image; perform analysis on at least one lesion in the high-resolution new image and the high-resolution reference image; and display a result of the analysis on a validator.

21 Claims, 15 Drawing Sheets

Related U.S. Application Data

(60) Provisional application No. 63/363,484, filed on Apr. 22, 2022.

(58) Field of Classification Search
CPC .................. G06T 2207/30004–30104; G06T 2207/30088; G06T 2207/30096; G06T 2207/10016; G06T 7/10–194; G06T 2207/20112–20168; G06T 2207/20016; G06T 7/30–38; G06T 7/70–77; G06T 7/60; G06T 7/62; G06T 7/64; G06T 7/66; G06T 7/68; G06T 2207/10024; G06T 7/90; G06V 2201/03–034; G06V 2201/032; G06V 10/25; G06V 10/26–267; G06V 10/24–248; G06V 10/75–761; G06V 10/56; A61B 5/44; A61B 5/441; A61B 5/442; A61B 5/443; A61B 5/444; A61B 5/445; A61B 5/446; A61B 5/447
See application file for complete search history.

(56) References Cited

U.S. PATENT DOCUMENTS

| | | | |
|---|---|---|---|
| 8,194,952 | B2 | 6/2012 | Mertz et al. |
| 8,337,405 | B2 | 12/2012 | Waagen et al. |
| 9,418,422 | B2 | 8/2016 | Daly et al. |
| 9,615,786 | B1* | 4/2017 | Roney .................. H04N 1/107 |
| 10,660,561 | B2 | 5/2020 | Bao et al. |
| 2007/0003117 | A1 | 1/2007 | Wheeler et al. |
| 2008/0095465 | A1 | 4/2008 | Mullick et al. |
| 2010/0232773 | A1* | 9/2010 | DePaula ............. A61B 5/6888 396/5 |
| 2015/0221087 | A1* | 8/2015 | Houjou .................... G06T 5/20 382/128 |
| 2017/0270667 | A1* | 9/2017 | Khazaeni ............. G16H 30/20 |
| 2017/0301080 | A1 | 10/2017 | Yan et al. |
| 2018/0122065 | A1* | 5/2018 | Abedini ................ G06T 7/0016 |
| 2018/0122076 | A1* | 5/2018 | Abedini ................ A61B 5/6898 |
| 2018/0357517 | A1 | 12/2018 | Gandenberger |
| 2019/0188853 | A1 | 6/2019 | Schirman et al. |
| 2019/0370970 | A1 | 12/2019 | Kim et al. |
| 2021/0166379 | A1 | 6/2021 | Smith |
| 2021/0166391 | A1 | 6/2021 | Hermosillo Valadez et al. |
| 2021/0228148 | A1* | 7/2021 | Rajak ................... A61B 5/4842 |
| 2022/0164957 | A1* | 5/2022 | Jia .......................... G16H 50/20 |
| 2022/0338805 | A1* | 10/2022 | Jeraj .................... A61B 6/5217 |
| 2023/0067762 | A1* | 3/2023 | Irrgang ................. G06T 7/0012 |
| 2023/0215096 | A1* | 7/2023 | Hall ...................... G06T 7/0012 345/419 |
| 2024/0020833 | A1* | 1/2024 | Ovchinnikova ..... G06V 10/774 |

OTHER PUBLICATIONS

C.-L. Tsai, H.-C. Hsu, X.-C. Wu, S.-J. Chen and W.-Y. Lin, "Accurate Joint-Alignment of Indocyanine Green and Fluorescein Angiograph Sequences for Treatment of Subretinal Lesions," in IEEE Journal of Biomedical and Health Informatics, vol. 21, No. 3, pp. 785-793, May 2017 (Year: 2017).*

International Search Report and Written Opinion dated Jul. 26, 2023 issued in International Application No. PCT/US2023/019637.

Tahata et al., "Evaluation of biodistribution of sulforaphane after administration of oral broccoli sprout extract in melanoma patients with multiple atypical nevi", Cancer Prev Res, AACR, 2018; 11(7):429e38-437.

Navarro et al., "Accurate segmentation and registration of skin lesion images to evaluate lesion change", IEEE Journal of Biomedical and Health Informatics, 2018; 23(2):501-508.

Farazi et al., "Inpainting Multiple Sclerosis Lesions for Improving Registration Performance with Brain Atlas", 2016 Int'l Conf. on Medical Engineering, Health Informatics and Technology (MediTec). IEEE, 2016:1-6.

Examination Report issued on Jan. 24, 2025 in corresponding Australian Patent Application No. 2023256612.

Thevenaz, P. et al, "A Pyramid Approach to Subpixel Registration Based on Intensity", IEEE Transactions on Image Processing, vol. 7, No. 1, Jan. 1998.

Zhou, F. et al., "A Coarse-to-Fine Subpixel Registration Method to Recover Local Perspective Deformation in the Application of Image Super-Resolution", IEEE Transactions on Image Processing, vol. 21, No. 1, Jan. 2012.

* cited by examiner

| Provider | Image Pair Type | Time Between Viewing Registered and Unregistered Images (d) | Number of Total Changes Detected | Number of New/Increased Lesions Detected | Number of Decreased/ Disappeared Lesions Detected | Number of Surgically Removed Lesions Detected | Number of Image Pairs with New/ Increased Lesions Detected |
|---|---|---|---|---|---|---|---|
| Dermatologist 1 | Unregistered | 21 | 158 | 117 | 30 | 11 | 14 |
|  | Registered |  | 244 | 203 | 25 | 16 | 18 |
| Dermatologist 2 | Unregistered | 10 | 75 | 46 | 17 | 12 | 16 |
|  | Registered |  | 82 | 57 | 11 | 14 | 15 |
| Dermatologist 3 | Unregistered | 40 | 48 | 28 | 6 | 14 | 13 |
|  | Registered |  | 75 | 56 | 10 | 9 | 16 |
| Medical Oncologist 1 | Unregistered | 1 | 10 | 2 | 3 | 5 | 2 |
|  | Registered |  | 37 | 23 | 8 | 6 | 13 |
| Medical Oncologist 2 | Unregistered | 0.167 | 84 | 61 | 11 | 12 | 14 |
|  | Registered |  | 183 | 121 | 46 | 16 | 17 |
| Total mean | Unregistered | 14.4 | 75.0 | 50.8 | 13.4 | 10.8 | 11.8 |
|  | Registered |  | 124.2 | 92.0 | 20.0 | 12.2 | 15.8 |
| Total SD | Unregistered | 16.6 | 54.6 | 43.0 | 10.7 | 3.4 | 5.6 |
|  | Registered |  | 86.0 | 71.5 | 16.0 | 4.5 | 1.9 |
| Fold Difference between Registered and Unregistered |  |  | 1.7 | 1.8 | 1.5 | 1.1 | 1.3 |

FIG. 14

METHOD FOR REGISTERING TWO OR MORE PATIENT IMAGES FOR CHANGE ASSESSMENT OVER TIME

CROSS REFERENCE TO RELATED APPLICATIONS

This application is a bypass continuation application of International Application No. PCT/US2023/019637 filed on Apr. 24, 2023, which claims priority to and the benefit of U.S. Provisional Patent Application No. 63/363,484, filed on Apr. 22, 2022, entitled A METHOD FOR REGISTERING PAIRS OF PATIENT IMAGES FOR CHANGE ASSESSMENT OVER TIME, which are expressly incorporated herein by reference in their entirety.

FIELD OF THE INVENTION

This disclosure generally relates to methods and systems of image processing that aligns locus between two or more images; and more particularly, methods and systems of alignment of skin lesions between two or more body images. This disclosure generally relates to early skin cancer detection methods and systems.

BACKGROUND

The practice of medicine often involves comparison of images, data, and/or anatomical features, such as a nevus or skin lesion, over time. Skin cancer screening evaluates lesions on the skin surface, including nevi and/or growths over time. Screenings may be conducted by a medical provider to evaluate and assess changes to the lesions, including new lesions, absence of old lesions, and/or changes to the physical characteristics of existing lesions, as these indications may be indicative of cancer. Medical providers may further assess the lesions for atypical color, size, shape, and/or texture.

Skins cancer screenings may be recommended for annual wellness and as a preventative care measure to detect cancerous growths before the progression to metastatic disease. Conventional skin cancer screening is a time-consuming process, as the medical provider conducts a physical examination of the patient's lesions. The patient typically returns for multiple visits to determine if any lesions have changed over time. The medical providers may then compare physical notes or static photographs, providing limited utility.

The assessment of changes to lesions in serial digital images is complicated by factors relating to the images themselves, including differences in scale, body habitus, posture, and lighting between the serial photographs. Factors relating to the human evaluator include differences in provider experience as well as time pressures posed by clinical workload and competing responsibilities. These issues contribute to the limitations of human perception of subtle changes in multiple lesions simultaneously under suboptimal conditions. For example, nevi are dynamic, but human reviewers will typically find minor or no change over time due to the inability to measure simultaneous subtle changes that still may be indicative of cancer. Thus, conventional methods of skin cancer screening often lead to late diagnosis or misdiagnosis of skin cancer. Accordingly, there is a need for objective and reproducible methods and systems to efficiently and accurately assess change in lesions.

BRIEF SUMMARY

The systems and methods of the present disclosure enable the registering of two or more patient images for change assessment over time. The methods and systems of the present disclosure may lead to objective and reproducible methods and systems to efficiently and accurately assess change in a lesion that may be common between two or more images.

The present disclosure relates to a method of registering two or more patients images for change assessment over time, comprising: obtaining a new image of an area with an image capture system; obtaining a reference image of a similar area; performing pre-processing of the new image and the reference image, wherein at least one point is determined in the new image that corresponds to at least one point in the reference image, and wherein a point is a centroid of at least one lesion; performing a coarse alignment of the new image and the reference image to coarse align the at least one point in the reference image and the at least one point in the new image to generate a point match; performing a high-resolution estimate to generate a high-resolution new image and a high-resolution reference image, wherein the high-resolution new image and the high-resolution reference image have an increased number of points; performing an alignment of the high-resolution new image and the high-resolution reference image, wherein the high-resolution new image and the high-resolution reference image have an increased number of point matches; cross-checking the at least one-point match to eliminate false matches and confirm correct matches of the high-resolution new image and the high-resolution reference image; performing segmentation of the high-resolution new image and the high-resolution reference image to distinguish at least one lesion from the area; performing analysis on the at least one lesion in the high-resolution new image and the high-resolution reference image; and displaying a result of the analysis on a validator.

The presently disclosed systems and methods may be embodied as a system, method, or computer program product embodied in any tangible medium of expression having computer useable program code embodied in the medium.

DESCRIPTION OF THE DRAWINGS

It is to be understood that both the foregoing summary and the following drawings and detailed description may be exemplary and may not be restrictive of the aspects of the present disclosure as claimed. Certain details may be set forth in order to provide a better understanding of various features, aspects, and advantages of the invention. However, one skilled in the art will understand that these features, aspects, and advantages may be practiced without these details. In other instances, well-known structures, methods, and/or processes associated with methods of practicing the various features, aspects, and advantages may not be shown or described in detail to avoid unnecessarily obscuring descriptions of other details of the invention.

The present disclosure may be better understood by reference to the accompanying drawing sheets, in which:

FIG. 14 is a table of change assessment for lesions detected by medical providers and the systems and methods of the present disclosure.

Note: FIGS. 10D through 10G are reproduced and altered from Tahata et al. (2018).

DETAILED DESCRIPTION

This disclosure generally describes systems and methods of registering two or more patient images for change assessment over time. The methods and systems of the present disclosure may lead to objective and reproducible methods and systems to efficiently and accurately assess change in a lesion that may be common between two or more images, such as a change in size, shape, color, or texture, and/or the appearance or disappearance of a lesion from at least one of the two or more images.

Figure 1:
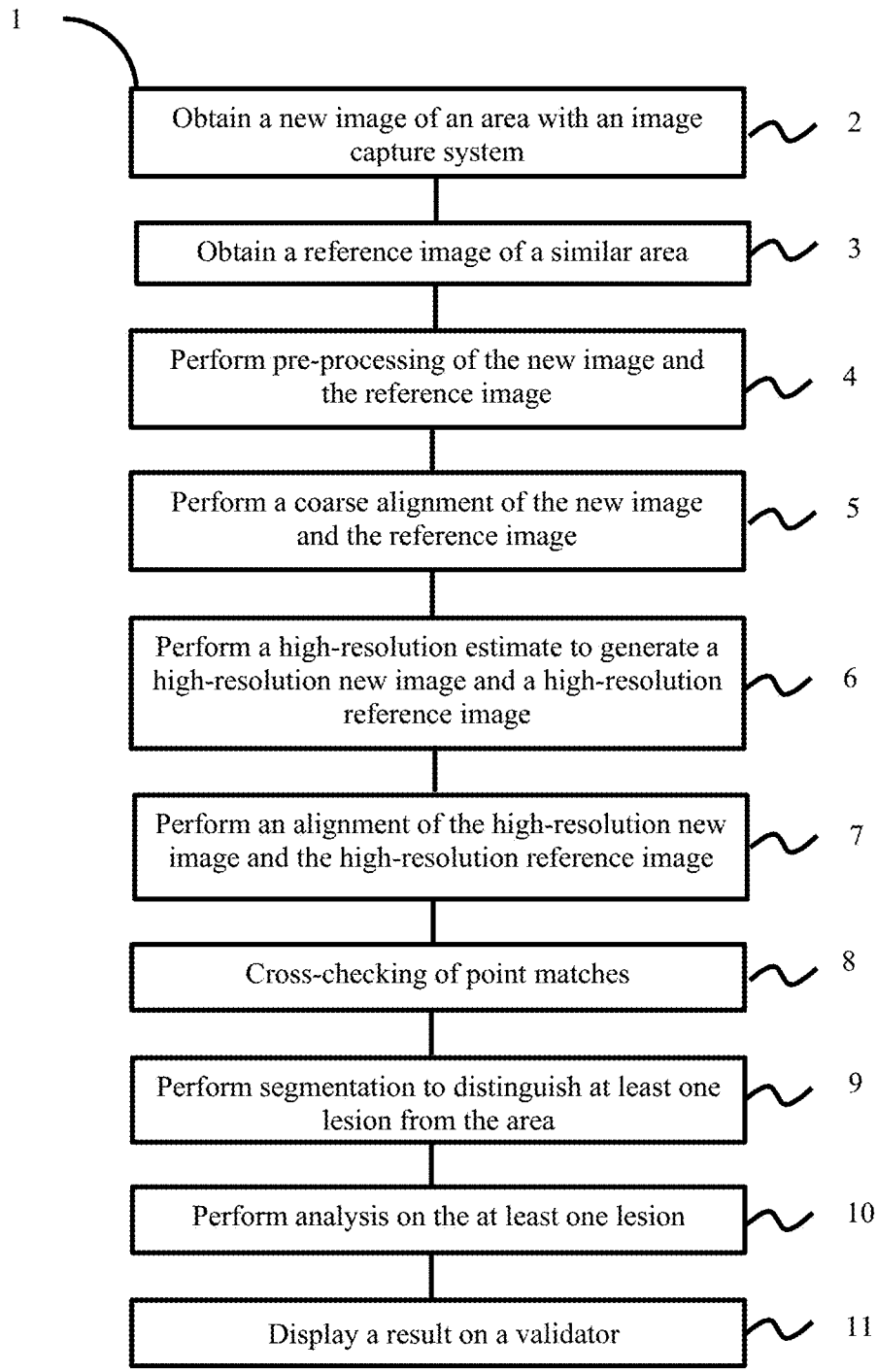
FIG. 1 is a flow chart of a method for registering two or more patient images for change assessment over time, in accordance with certain aspects of the present disclosure.

The present disclosure provides a method 1 (FIG. 1) for registering two or more patient images for change assessment over time. The method 1 may obtain a new image of an area of a patient with an image capture system 2. An image capture system may include, but is not limited to, any device capable of obtaining an image from a sensor, such as a camera, smartphone, computer, tablet, medical imaging machines such as CAT scanners, nuclear magnetic resonance imaging machines, x-ray machines, microscopy and/or endoscopy imaging equipment, astronomical surveying equipment, and satellite and/or aerial photograph systems. The image capture system may be provided by the patient or the medical provider. The image capture system may comprise a panoramic image capture system capable of obtaining a panoramic view of an area. The image capture system may further comprise a 360-degree image capture system capable of capturing a 360-degree image. Thus, an image of the present disclosure may comprise a panoramic image or a 360-degree image.

The method 1 may obtain a reference image of a similar area of a patient 3. The reference image may be an image previously taken at any point in a patient's life. Thus, a reference image is any image captured at a time before the new image was captured. While conventional image comparison systems and methods require advanced image acquisition devices in order to obtain a new image and a reference image, the methods and systems of the present disclosure may be used to retrospectively compare archival images. The methods and systems are device agnostic: as long as the new image is of a sufficiently similar area compared to the reference image, the methods and systems of the present disclosure may accurately assess change in at least one lesion of the new and reference images over time. Thus, the new image and the reference image do not need to be identical.

Conventional image comparison methods may assess change through serial dermoscopy of single-pigmented lesions. However, the pigmented lesions of concern must be prespecified by physicians before they may be evaluated through dermoscopy. Such focused assessment will miss changes in lesions that were not specifically selected for baseline imaging. However, the methods and systems of the present disclosure allows for images of an area of a patient comprising the entire skin surface of a patient. The method 1 may combine or "stich" at least two poses of skin images to obtain a complete or partial skin surface of a patient. The method 1 may align and compare patient images of any skin tone, including, but not limited to, Fitzpatrick Type I, Type II, Type III, Type IV, Type V, Type VI, any combination thereof, and the like. The methods and systems permit tracking of multiple lesions within the images while computing an accurate relative change between the images.

A reference image may be obtained from any database or image storing system capable of storing an image. In some aspects, the method 1 may obtain a new image from a database. Thus, a new image may be any image that is captured at a time after the reference image was captured.

A sufficiently similar area may include at least 40% overlap in area between the new image and the reference image, including, without limitation, at least 50%, 60%, 70%, 80%, 90%, 95%, and at least 99% overlap. Any combination of lower and upper limits may define a sufficiently similar area, such as, 40%-50%, 50%-60%, 60%-70%, 70%-80%, 80%-90%, and 90%-99% percent overlap. The methods and systems of the present disclosure may accommodate resolution ratios as disparate as 1:3 linear, 1:9 area, and/or angular rotations of ±10 degrees along with mild keystoning and additional translation shifts, wherein keystoning is defined by the angle θ between the plane of the camera and the plane of the image being captured, wherein θ=0 occurs when the camera plane and the patient's skin region are parallel. The severity of keystoning may be dependent upon the biological presentation of the lesion and identifiable landmarks. For typical skin biological presentations, the systems and methods of the present disclosure may resolve keystoning up to 10 degrees, including, without limitation, 9, 8, 7, 6, 5, 4, 3, 2, 1, and 0, including, without limitation, 0-1, 0-2, 0-3, 0-4, 0-5, 0-6, 0-7, 0-8, 0-9, and 0-10 degrees.

Conventional methods of assessing images for change over time require the patient to be in the same posture, be the same distance from the image capture system, have the same lighting, and/or have the same image capture system for the new and reference images. The methods and systems of the present disclosure may accommodate new and reference images of a patient in a different posture, a different distance from the image capture system, a different amount of lighting, and of a different image capture system. Moreover, the methods and systems of the present disclosure may also accommodate new and reference images of a patient who has gained or lost weight, experienced a significant change in skin tone, such as a suntan or sunburn, undergone cosmetic surgery, or added or removed body art such as a tattoo, piercing or permanent cosmetic. Accordingly, the methods and systems of the present disclosure are invariant to global changes in scale and translation. Furthermore, the methods and systems are invariant to local and global changes in rotation, translation, lighting, warping, and the like.

The method 1 may perform pre-processing of the new image and the reference image 4. Pre-processing may comprise segmentation, wherein the reference image and the new image are segmented to exclude background of the image. For example, when the new and reference images are of a skin area, the background may be the areas of skin wherein no lesions are present. Thus, segmentation may distinguish a lesion from the background skin. Segmentation may also define an outline of a patient's body to remove all environmental features that are not a part of the patient's body. Pre-processing may comprise cropping an image to remove areas of the body or the environment of the patient that are not of interest to be analyzed.

While performing pre-processing is not necessary, it may be preferable to decrease the overall area of the new and reference images to be processed for alignment. Segmentation may comprise converting the red-green-blue image of the new and reference images into three separate images for hue, saturation, and intensity for both the new and reference images. Lesion filtering-threshold methods for each of the hue, saturation, and intensity domains may be applied individually. The three images may be recombined to create a unified segmentation of the lesion/skin boundary for the new image and the reference image.

During pre-processing, the method 1 may determine at least one point in the new image and the reference image. A point may be a centroid, or the center of mass of a lesion. The method 1 may individually analyze the new and the reference image to identify points within an area. A lesion may occupy more than one pixel. Thus, the method 1 may locate the centroid of each lesion to identify at least one point in both the new image and the reference image.

A centroid may shift as a lesion changes over time. Thus, a centroid of a lesion that is common between the new image and the reference may be shifted in the new image relative to the reference image due to growth over time. However, a smaller lesion tends to change on a smaller scale compared to a larger lesion over time. Accordingly, the method 1 may selectively choose lesions and/or landmarks that are small and do not exhibit change from the reference image to the new image to determine points in order to provide a more precise alignment of the images. Landmarks may include discrete points or loci of correspondence or equivalency among organisms. Small lesions and/or landmarks may include, but are not limited to, lesions and/or landmarks having a diameter of 0.1 mm to 3 mm. Accordingly, small may comprise any lesion having a diameter less than 3 mm, such as less than 2.5, 2.0, 1.5, 1.0, 0.9, 0.8, 0.7, 0.6, 0.5, 0.4, 0.2 mm, and a diameter of at least 0.1 mm, such as at least 0.2, 0.3, 0.4, 0.5, 0.6, 0.7, 0.8, 0.9, 1.0, 1.5, 2.0, and at least 2.5 mm. The method 1 may ignore large lesions or lesions that exhibit growth or disappear over time, as they may provide a less precise alignment due to a more significant shift in the location of the centroid between the reference image and the new image. Large lesions and/or landmarks may include, but are not limited to, lesions and/or landmarks having a diameter of greater than about 3 mm, such as greater than 4 mm, or 5 mm. Accordingly, large may comprise any lesion having a diameter of at least 3 mm, such as at least 3.0, 3.5, 4.0, 4.5, 5.0, 5.5, 6.0, 6.5, 7.0, 7.5, 8.0, 8.5, 9.0, 9.5, and at least 10.0 mm.

The method 1 may perform a coarse alignment of the new image and the reference image to coarse align at least one point in the reference image to at least one point in the new image 5. The method 1 may find an estimate of scale and rotation of one image in respect to the other. This may include estimates of the angle and/or orientation of each image. For example, one image may have a different orientation or scale than the other. Thus, the method 1 may determine the degree of rotation or amount of rescaling necessary and perform the rotation and rescaling to generate images that may be more precisely aligned and more uniform in overall shape.

The coarse estimate may comprise any appropriate technique, process, or system for approximately aligning the images, such as conventional image alignment techniques. The coarse estimate may include linear transformation of the new image or reference image with respect to the other to generate coarsely aligned images. Linear transformations may include, but are not limited to, rotation, scaling, translation, and other fine transforms. The method 1 may use the coarse estimate to approximately align the images so that differences between the images are minimized, allowing for more accurate alignment at later steps.

The coarse estimate may employ feature-based methods for image registration, comprising finding a correspondence between image features, including, but not limited to, points, lines, and contours. Geometrical transformation may be performed when knowing the correspondence of a number of points in the images to map the target image to the reference image, which may establish a point-by-point correspondence between the reference and target image.

During coarse alignment, the reference image and the new image may be processed and/or coarse aligned separately. The method 1 may distribute the points within each image in a 2×2 matrix, wherein the distance of each point relative to another point may be calculated. Distance, as used herein, may refer to pixels or any other measurement capable of measuring distance between two points in an image. The angle and distance of diagonal elements may be calculated. The angle measurement of two points within an image may be doubled and then computed by modulo operation 2*pi or 360 degrees and encoded by the method 1. Only one angle for each pair of points needs to be calculated. For example, if the angle of point 1 to point 2 is 30 degrees, the angle is doubled to 60 degrees, remains 60 degrees when computed modulo 360 degrees, and may be encoded as 60 degrees. The corresponding angle of point 2 to point 1 of 210 degrees may be doubled to 420 degrees. When computed modulo 360 degrees, 420−360=60 degrees. Thus, the angle may be encoded as 60 degrees. Accordingly, the method does not require an absolute ordering of the points, and the encoding process is independent of ordering. In the new image, point 1 may precede point 2, while in the reference image, point 2 may precede point 1.

The method 1 may then calculate the logarithm of the distance between two points and plot the points in a 2×2 2-dimensional array, wherein the logarithm of distance is the horizontal axis, and the angle is the vertical axis. When the invention encodes a point, a weighting using the interpoint distance may be utilized in encoding the two matrices that represent angle and distance calculations.

Once the 2×2 array is plotted for both the reference image and the new image, correlation may be performed until the points of both images overlay through the method of convolution. While a square matrix having a specific dimension has been described, other dimensions and shapes are possible and within the scope of the present disclosure.

The method of convolution may be any method generally known in the art. Convolution may multiply the array of the new image and the array of the reference image, generally of different sizes, but of the same dimensionality, to produce a third array of numbers of the same dimensionality. Convolution of the 2-dimensional arrays may obtain the offset of the new and reference images in logarithm and angle. The offset in angle may be halved to obtain the rotation of the new image with respect to the reference image or the rotation of the reference image with respect to the new image.

The method 1 may calculate a peak in 2-dimensional space, which represents the difference between the logarithms of distance from two points. Thus, the method 1 may calculate the exponential of the difference from the two points to determine scale. The method 1 may further determine angular difference from two points using convolution. Accordingly, the method 1 may determine scale and rotation without associating specific points within the new image and the reference image. As such, intra-image data may determine rotation and scale.

The method 1 may then estimate where points in the new image and the reference image overlap. The method 1 may use a matching algorithm to find the best point matches. The matching algorithm may comprise any technique that finds matching points of the new image and the reference image.

The method 1 may then perform the matching at least a second time until a desired level of matching is reached. The method 1 may calculate an error in the matches for each matching step. A desired level of matching may occur when there is no additional improvement in reducing error. The method 1 may generate an overall coarse image of the new image and the reference image. The method 1 may then transform the coarse images at low resolution to produce coarse images at low resolution. The transformation at low resolution may comprise further point matching and non-linear mapping, including but not limited to, image warping. Image warping may be used to correct image distortion at low-resolution. As used herein, the term "warping" refers to the distortion of a static image to produce another static image. Typically, warping is understood to include transformations that only affect some of the pixels in an image rather than all of them.

The method 1 may then perform a high-resolution estimate by transforming the coarse images to generate a high-resolution new image and a high-resolution reference image 6. The method of transforming the coarse images may comprise any transformation method as described above, including, but not limited to, non-linear mapping or warping. The high-resolution new image and high-resolution reference image may comprise an increased number of points identified within each image. The method 1 may then perform an alignment of the high-resolution new image and the high-resolution reference image 7, wherein the alignment may generate an increased number of point matches. The method 1 may divide the images into nine tiles with overlap. Starting at the tile with the most point matches, the method 1 may process each tile one at a time, generating more point matches. Processing may include transformations such as non-linear mapping or warping, and point matching, providing more points within each tile. All points may then be processed by a matching algorithm to remove mismatching and maximize the number of matched points, generating a set of control points. While the presently disclosed method 1 is described as dividing the images into nine tiles with overlap, other divisions are possible and within the scope of the present disclosure.

The method 1 may map the images according to user preference. For example, the method may warp the new image to match the references image, or the method may warp the reference image to match the new image. Typically, a health care provider may prefer to look at a new image that is not warped.

The high-resolution estimate generates high-resolution images of the new image and the reference image, wherein the images have an increased number of points and point matches compared to the images generated by coarse alignment. The method 1 may generate a list of paired points comprising points from the new image that match points from the reference image.

The method 1 may cross-check the point matches in the high-resolution images to eliminate false matches and confirm correct matches 8. The method 1 may continuously check for errors through each step. An error may include, but is not limited to, an incorrect match or any instance that may lead to an incorrect match.

Figures 10A, 10B, 10C:
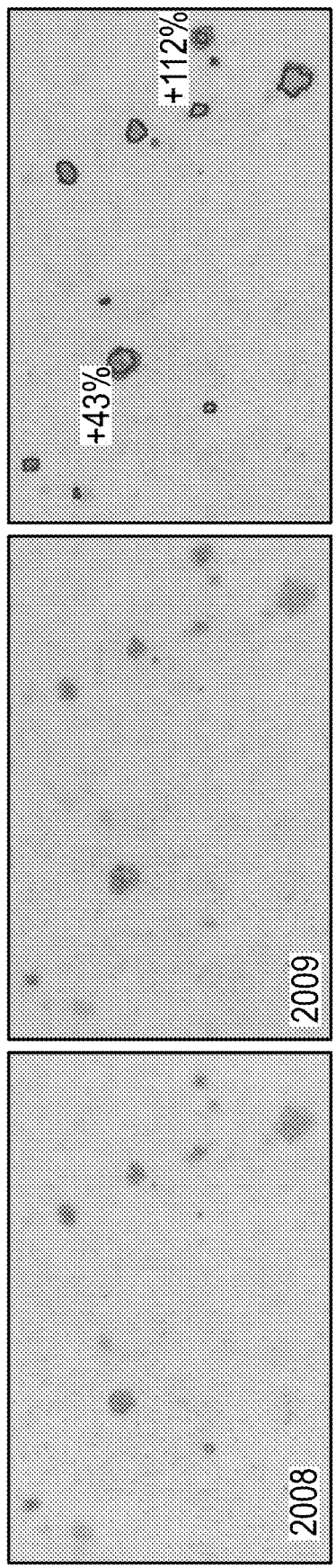
FIG. 10A is a reference image taken at a certain time point according to the methods and systems of the present disclosure.
FIG. 10B is a new image taken at a subsequent time point after registration and alignment according to the methods and systems of the present disclosure.
FIG. 10C is overlaid segmentation boundaries and example change quantification according to the methods and systems of the present disclosure.

The method 1 may perform the coarse alignment, the high-resolution alignment, and the cross-checking at least a second time until all point matches are correctly matched. Correctly matched, as used, herein may refer to at least 60% of the point matches have a corresponding centroid on the new and references images, including, without limitation, at least 60%, 70%, 80%, 90%, 95%, and at least 99%. Any combination of lower and upper limits may define correctly matched, such as, 60%-70%, 70%-80%, 80%-90%, 90%-95%, and 95%-99%, In order to analyze change in a lesion of the high-resolution new image and the high-resolution reference image over time, the method 1 may perform segmentation a second time to distinguish at least one lesion from the skin area 9. The first segmentation step described above analyzed similarities of lesions in both the new image and the reference image in order to facilitate a more correct alignment of the images. After images are correctly aligned, the second segmentation step may look for differences in lesions to distinguish each lesion from the skin area. The segmentation may aid in identifying inconsistencies between the lesions of the aligned images (FIG. 10C). The segmentation may occur between the reference image (FIG. 10A) and the new image taken at a subsequent time point after registration and analysis (FIG. 10B).

The method 1 may then perform analysis on at least one lesion of the aligned high-resolution reference and high-resolution new images 10. The analysis on at least one lesion of the aligned high-resolution reference image and the high-resolution new image may comprise analyzing each image individually. Performing analysis on a lesion may comprise calculating size features of a lesion, including, but not limited to, area, diameter, and perimeter.

The method may use the binary mask of the nevus in a feature cue and the size information from an image ruler 500 to compute feature values. An image ruler 500, as used herein, may comprise any device with at least one marking 510 capable of measuring or displaying a measurement of a lesion. Markings 510 may measure distance in any unit of measurement, including, but not limited to, millimeters, centimeters, inches, and the like. An image ruler 500 may comprise color swatches 530 to measure color and/or markings denoting distance. The color swatches 530 may comprise at least two individual rectangles or at least two rectangles connected to one another to form a color gradient. The color swatches 530 may represent the range of colors expected in an image of skin, including possible lesion coloring. In some aspects, the ruler 500 may comprise two rows of color swatches 530. The color swatches 530 may standardize color across images of different dates and lighting conditions. The image ruler 500 may be placed on the area that is to be photographed by the image capture system in at least one of the new image or the reference image to determine a measurement of a lesion according to the methods and systems of the present disclosure. Thus, the ruler 500 may be placed on the skin of a patient prior to capturing the new image and/or the reference image. The ruler 500 may comprise text and spaces for the placement of medical information, including, but not limited to, patient ID, patient name, date, and the like.

A ruler 500 with color swatches 530 may be placed on the area that is to be photographed by the image capture system in both the new image and the reference image to determine a measurement of color and change in color according to the methods and systems of the present disclosure. If a ruler does not comprise color swatches 530 as described above, the method 1 may assume skin tone is unchanged.

If a ruler 500 is not present in either the new image or the reference image, the method 1 may calculate size changes as a percentage or as a pixel measurement, wherein the method 1 may measure diameter, area, border, and/or the like of a lesion according to the number of pixels. In order to assess the measurement of a lesion in terms of a unit of measurement such as millimeter, the user may enter the scale of the new image and the reference image.

Figure 10G:
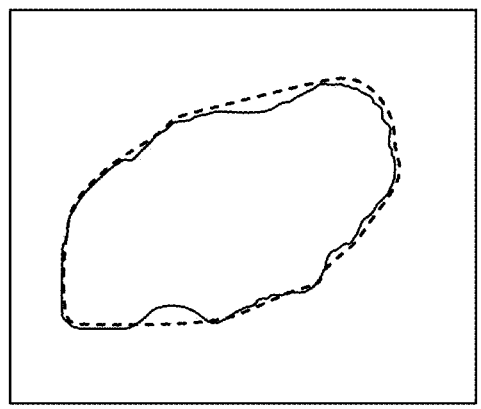
FIG. 10G is the delineation of a convex hull of a lesion according to the methods and systems of the present disclosure.
Figure 10F:
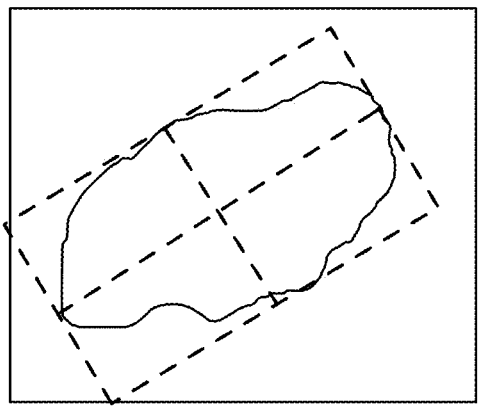
FIG. 10F is the delineation of major and minor axes of a lesion according to the methods and systems of the present disclosure.
Figure 10E:
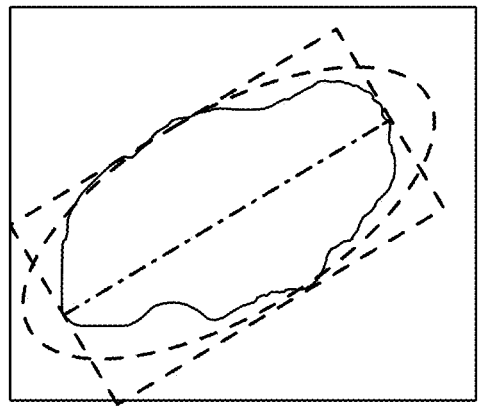
FIG. 10E is the delineation of diameter of a lesion according to the methods and systems of the present disclosure.

Area may be calculated in square millimeters using the pixels within the border of a lesion. The diameter (FIG. 10E) may be calculated using the major axis of the ellipse with the same second moments of inertia as the lesion, wherein the diameter is the extent of the lesion along its major axis, measured in millimeters. The perimeter is the measure of the distance around the border of the lesion in millimeters.

Two features of folding asymmetry may be calculated from the mask that has been folded along the major and minor axis (FIG. 10F) of the lesion in order to capture the asymmetry of the lesion's shape. The method may divide the mask into quadrants along the major and minor axis of the lesion to capture the asymmetry of the lesion's shape, which may generate three features of quadrant asymmetry.

Figure 10D:
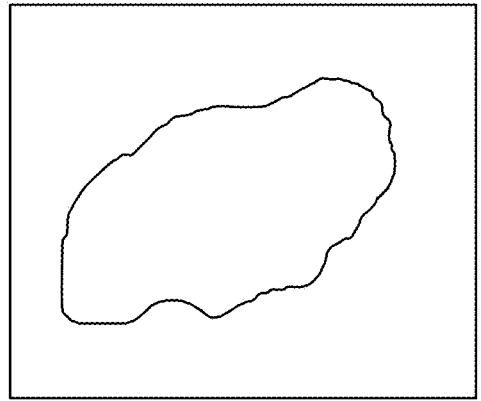
FIG. 10D is the delineation of border of a lesion according to the methods and systems of the present disclosure.

The method may delineate the border of a lesion (FIG. 10D). The method may calculate four border features from a gap mask, which may be defined as the difference of the lesion mask and the convex hull (FIG. 10G) of the lesion mask, to capture the border irregularity of the lesion's shape. The gap mask may be divided into quadrants using the major and minor axis of the lesion.

Performing analysis on a lesion may comprise calculating color features of a lesion. The method 1 may use the color corrected image mapped into hue, saturation, and intensity obtained from the second segmentation step, color space, and the binary mask of the lesion in a feature cue to calculate color feature values. The method may calculate two features from the hue image to describe the color of the lesion. Hue is a circular variable, and the computation may use the standard definitions for a circular variable. The two features may include mean hue of pixels in a lesion and the standard deviation of hue of pixels in the lesion.

The method may calculate two features from the saturation image to describe the asymmetry of the color the lesion according to the saturation image. The method may then calculate two features from the intensity image to describe the asymmetry of the color of the lesion according to the intensity image. The hue image may also calculate one feature to describe the asymmetry of the color of the lesion.

Performing analysis may also comprise using the mask and color feature values computed for each feature cue in a new image and a reference image to compute the change that occurred between the two images. The block first matches feature cues. For cues that exist in the new image but not in the registered reference image, the lesion is considered de novo, which may be diagnostically significant cues. For cues that exist in the registered reference image, but not in the new image, the lesion is considered to have disappeared, which may be significant findings for judging therapeutic efficacy of a treatment of a suspect lesion. For cues that exist in both images, the raw change (simple difference) and percent change may be computed. The raw change and percent change of each lesion may be presented to a user such as a medical provider on a validator, wherein the medical provider may categorize the change values as none, minor, moderate, significant. The level of change required for each category may change depending on user preference.

Counts of cues in each category may be used to capture the overall change in the image. Medical providers may access the change in all individual lesions as well as the overall change in the image and the list of de novo and disappeared lesions.

When a lesion is a nevus and the new and reference image are being compared for purposes of the detection of skin cancer, the method 1 may analyze the images for features of melanoma, including, but not limited to, Asymmetry, Border irregularity, Color, Diameter, and Evolution (ABCDE).

The method 1 may then display a result on a validator 11. Displaying the result on a validator 11 may comprise any graphical user interface. The validator may be any program, application, or graphical display capable of classifying and characterizing lesions detected and analyzed by the methods and systems of the present disclosure. The validator may be configurable and allow for specific prompts and responses to be modified on the basis of user preference and the objectives of the study or medical use for which the systems and methods of the present disclosure are being used for. The validator may comprise a lesion manual identification (FIG. 11) wherein a medical provider may click on the centroid of each nevus to verify the accuracy of the method 1. The validator may comprise a nevus pair description (FIG. 12), wherein a medical provider may assess the accuracy of lesion registration between time points and identify the lesion at each time point through options on a drop-down menu. A drop-down menu may comprise a menu to select whether there is registered lesion overlap. The validator may comprise a ruler 500 on the graphical display to demonstrate measurements of the lesion. A ruler 500, as used herein, may comprise any device with at least one marking 510 capable of measuring or displaying a measurement of a lesion, including, if applicable, color swatches 530 to measure color.

Figure 13:
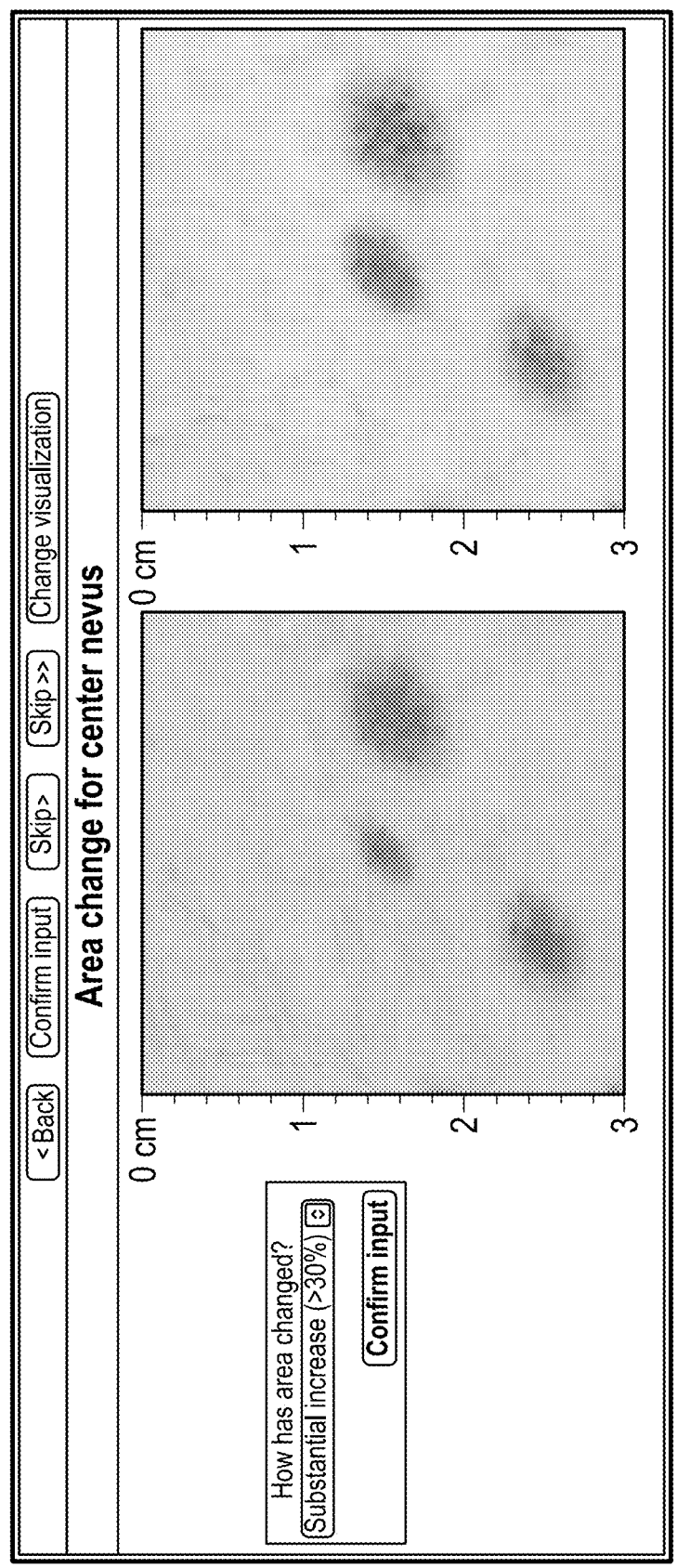
FIG. 13 is a screenshot view of a validator displaying area change according to an aspect of the present disclosure.

The validator may display area change for the centroid of a lesion, wherein a clinician may enter a subjective opinion of size change along a prespecified scale through a drop-down menu (FIG. 13). A user may input the level of change the user considers to be meaningful, and the methods and systems of the present disclosure may analyze the lesions and images according to a level of change or category of change input by the user. Categories of change may include, but are not limited to, substantial increase, intermediate increase, small increase, greater than 10% increase, greater than 20% increase, greater than 30% increase, greater than 40% increase, greater than 50% increase, greater than 60% increase, greater than 70% increase, greater than 80% increase, greater than 90% increase, greater than 100% increase, less than 5% increase, less than 10% increase, less than 20% increase, less than 30% increase, less than 40% increase, less than 50% increase, less than 60% increase, less than 70% increase, less than 80% increase, less than 90% increase, less than 100% increase, any combination thereof, or any combination of upper and lower limits, including but not limited to, 10%-20% increase, 20%-30% increase, 30%-40% increase, 40%-50% increase, 50%-60% increase, 60%-70% increase, 70%-80% increase, 80%-90% increase, and 90%-100% increase. Thus, the methods and systems of the present disclosure enable the detection of lesion pairs with significant change, which may be a change greater than at least 30%. Increase may be considered any change between a measurement of a lesion over time as measured and analyzed by the systems and methods of the present disclosure. The method 1 may analyze change over time as a percentage and/or a measurement of change depending on user preference.

Categorization may also include, but is not limited to, decreased, disappeared, surgically removed, increased, appeared, a new lesion, a pre-existing lesion that is absent, and/or a change in a pre-existing lesion such as a change in color, shape, dimension, border, and/or the like.

Figure 12:
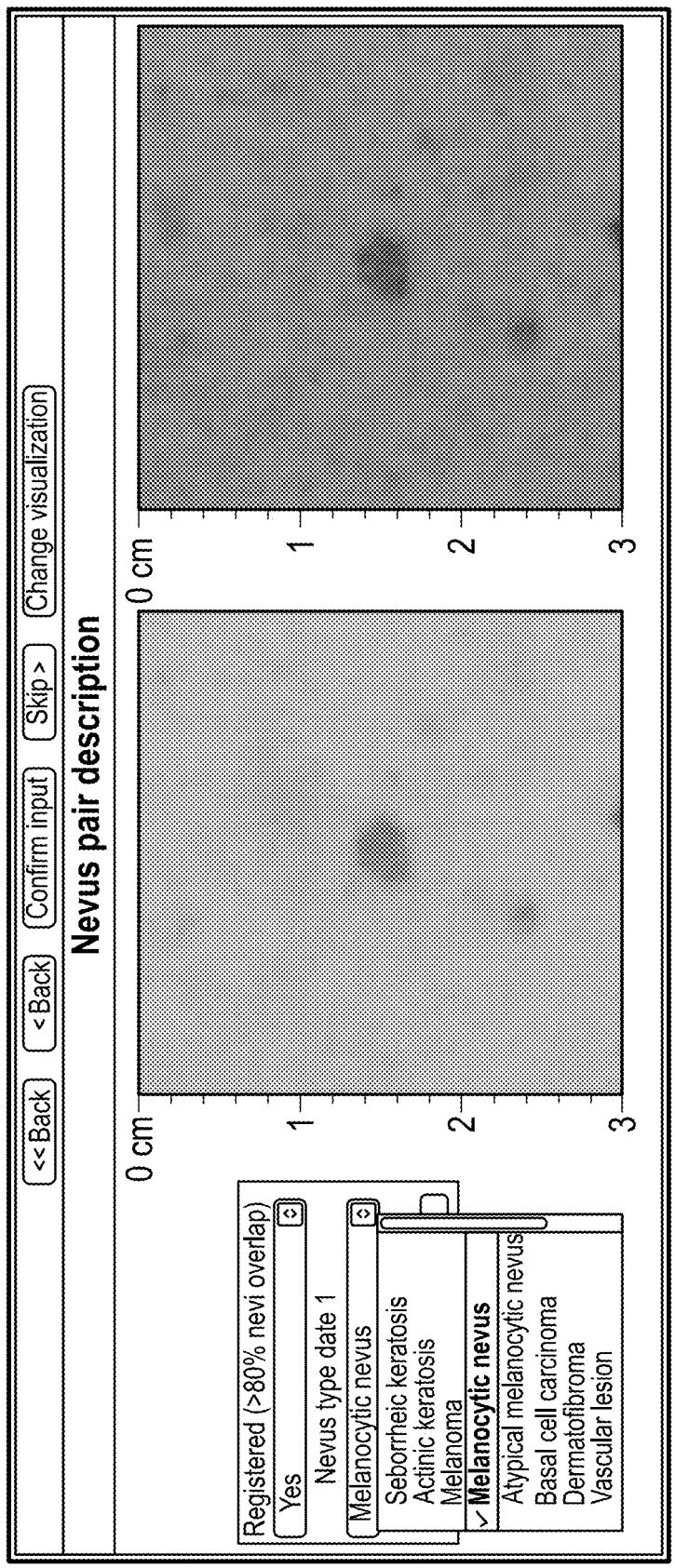
FIG. 12 is a screenshot view of a validator with lesion pair description according to an aspect of the present disclosure.

The validator of the systems and methods of the present disclosure may classify the lesions by type, including, but not limited to, melanocytic nevus, seborrheic keratosis, actinic keratosis, melanoma, melanocytic nevus, atypical melanocytic nevus, basal cell carcinoma, dermatofibroma, and vascular lesion (FIG. 12). The method 1 may identify nonmelanocytic structures and suspect artifacts such as dust on a camera lens.

The method 1 may calculate the total size change of all lesions combined between the reference image and the new image, which may aid in the early detection of skin cancer in a patient. Thus, the validator may analyze and display the total size change of all lesions combined between the reference image and the new image. The method 1 may perform statistical analysis of the change across all lesions, including, but not limited to, mean, median, and standard deviation.

The validator may stitch together the new image and the reference image to generate a 3-dimensional model of the patient's body with illumination of the detected changed lesions. This view may be beneficial compared to conventional views, as it gives a user or medical provider a 3-dimensional anatomical view of the lesions.

The method 1 may utilize the analysis of change in at least one lesion over time to calculate and display a probability of cancer for a patient. The probability of cancer may indicate the probability of a patient currently having cancer, even if undetected, or a probability of a patient developing cancer in the future.

The validator may generate a user number of an unknown user or collect and require a user to input login information for repeated use by the same user. The validator may collect registration data for a user or a patient, including, but not limited to, patient name, height, weight, medical history, gender, age, provider information, treatment history, address, and any other biometric data, physical characteristic, or historical information that may be useful to a medical provider.

The validator may generate a report to a user or medical provider. The report may be based on the analysis and comparison of aligned lesions of the new image and the reference image. The report may identify lesions that have changed based on predetermined criteria between the new image and the reference image. The report may include detailed images or zoomed in images of the lesions identified by the methods and systems of the present disclosure. The report may comprise locations and/or descriptions of each lesion.

A location of a lesion may comprise any method of describing a location, such as a measurement of the location of the skin feature using anatomical landmarks like shoulder blades and joints and/or describing the location relative to the location of other lesions. The description of a lesion may comprise the categorization or raw measurements as described above.

In order to provide an easier comparison of the new image and the reference image for the medical provider, the method 1 may flicker the new image and the reference image back and forth. As used herein, the term "flicker" refers to any switching or toggling back and forth within the same frame. The flickering of the images enables the static change over time to become dynamic and easier to be visualized by a medical provider. The speed of flickering may be changed dependent upon user preference.

Figure 2:
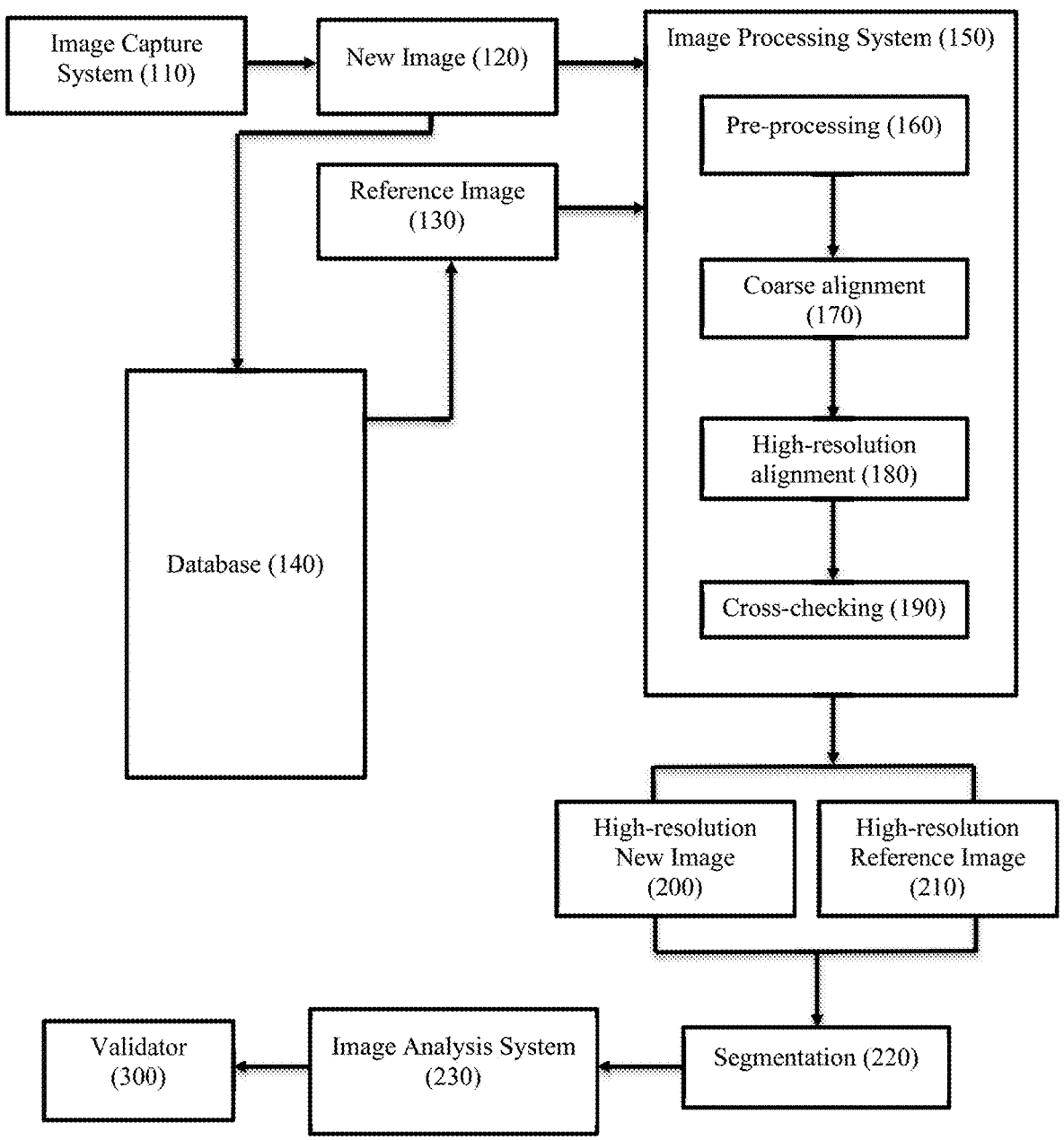
FIG. 2 is a schematic diagram of a system for registering two or more patient images for change assessment over time, in accordance with certain aspects of the present disclosure.

FIG. 2 is a block diagram that schematically illustrates a system 100 of the present disclosure for registering two or more patient images for change assessment over time. The system 100 may comprise an image capture system 110 configured to obtain a new image 120. An image capture system 110 may include, but is not limited to, any device capable of obtaining an image from a sensor, such as a camera, smartphone, computer, tablet, medical imaging machines such as CAT scanners, nuclear magnetic resonance imaging machines, x-ray machines, microscopy and/or endoscopy imaging equipment, astronomical surveying equipment, and satellite and/or aerial photograph systems.

The new image 120 generated by the image capture system 110 may be stored in a database 140. The database 140 may store at least one reference image 130 for alignment and analysis according to the methods and systems of the present disclosure. The new image 120 and the reference image 130 may be individually processed by an image processing system 150. The image processing system 150 may perform pre-processing 160, coarse alignment 170, high-resolution alignment 180, and cross-checking 190 according to the methods of the present disclosure, resulting in a high-resolution new image 200 and a high-resolution reference image 210. The system 100 may perform segmentation 220 of both high-resolution images to distinguish a lesion from a patient's skin.

Figure 15:
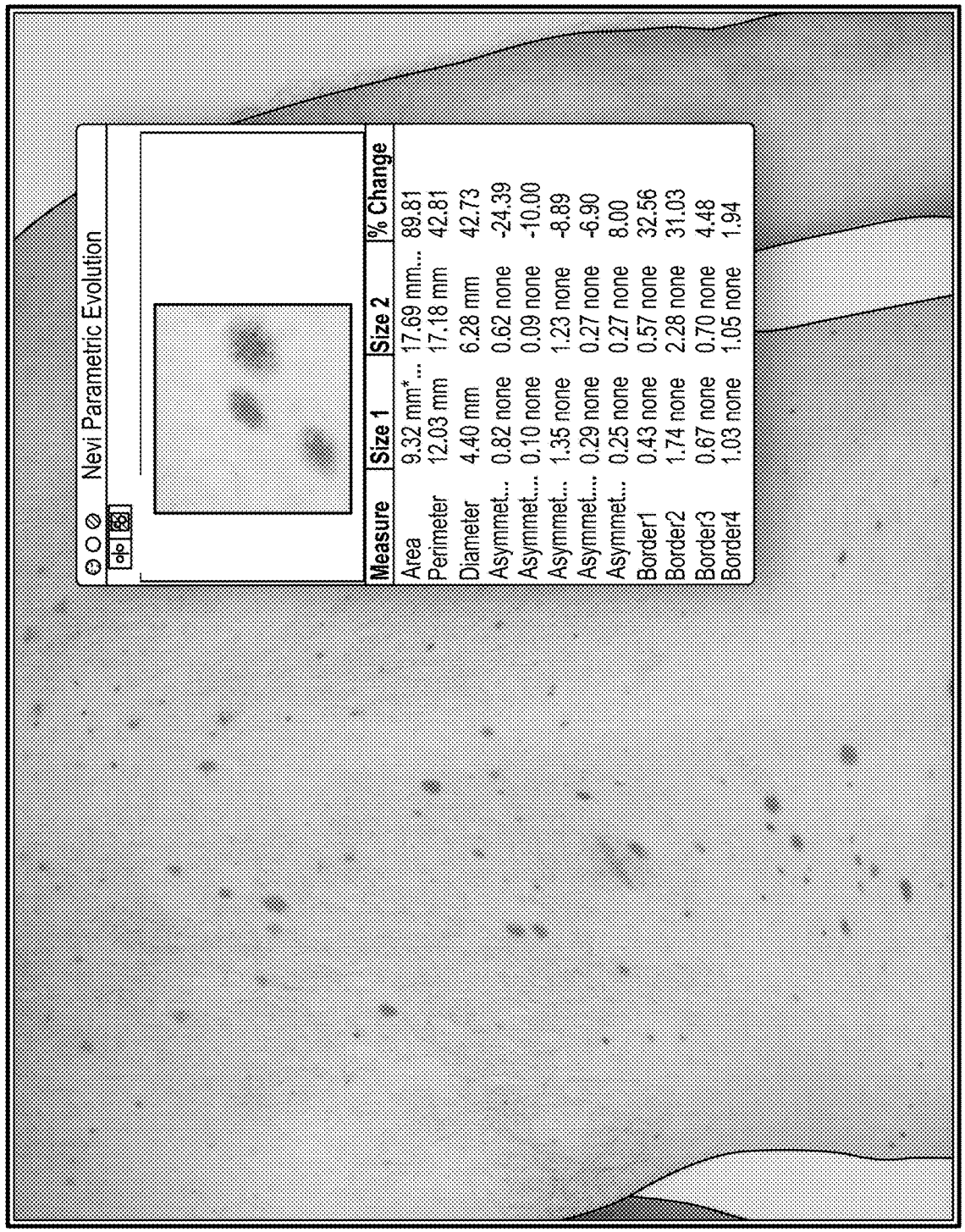
FIG. 15 is a screenshot view of a validator displaying measurements of at least one lesion and the percent change between the new image and the reference image according to the methods and systems of the present disclosure.

The image analysis system 230 may perform analysis on each lesion of the reference image and the new image resulting from segmentation 220 according to the methods and systems of the present disclosure. The system 100 may display the results on a validator 300, according to the methods described herein. Results may include a percent change of a measurement over time, raw measurement data, or any other display generated by the system 100 or method 1 (FIG. 15).

Figure 3:
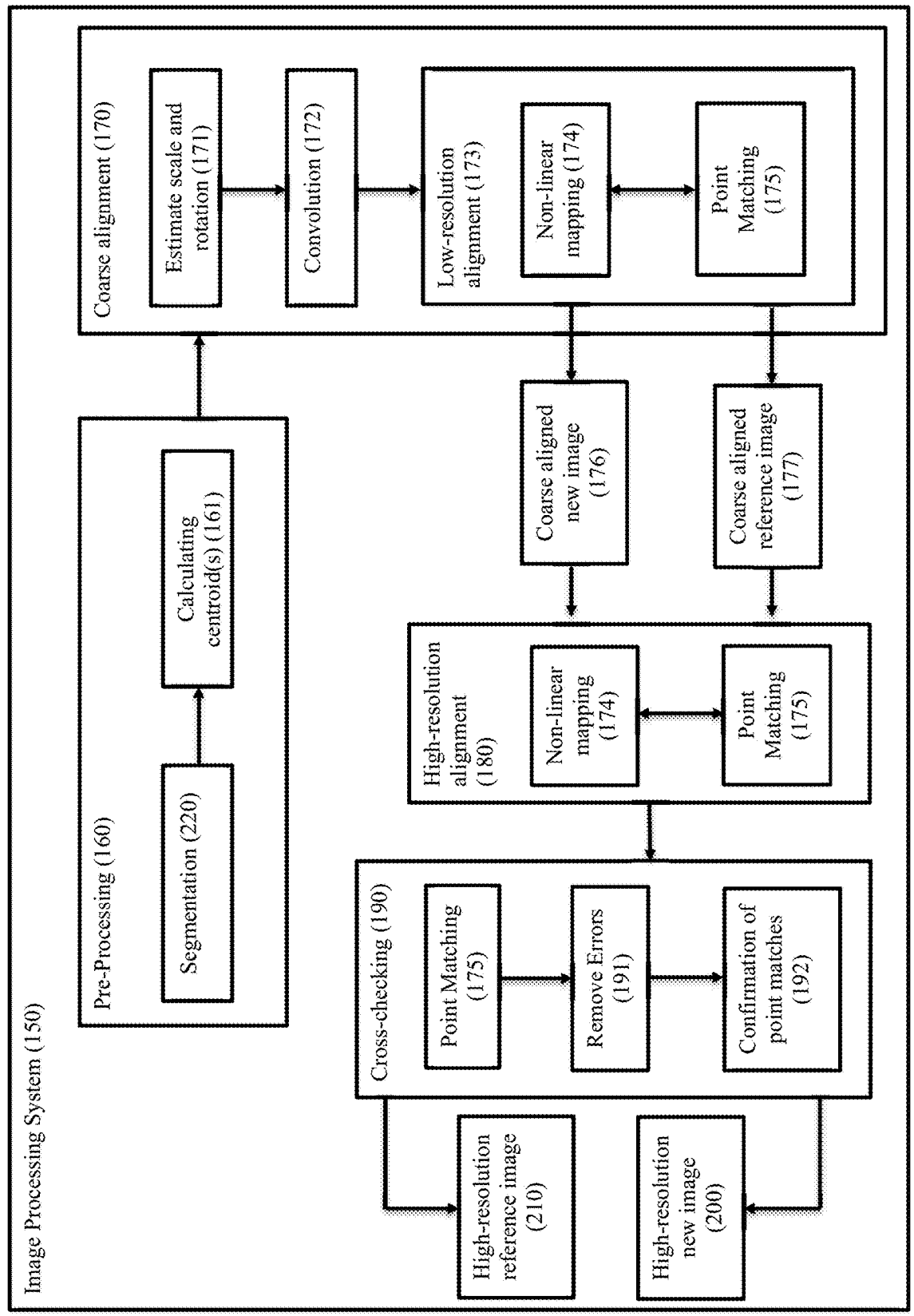
FIG. 3 is a schematic diagram of an image processing system in accordance with certain aspects of the present disclosure.

FIG. 3 depicts a block diagram of the image processing system 150. The image processing system 150 may comprise program instructions for pre-processing 160 the new image 120 and the reference image 130. Pre-processing 160 may comprise program instructions for segmentation 220 and calculating at least one centroid 161 of at least one lesion within the new image 120 and the reference image 130 according to the methods of the present disclosure. The image processing system 150 may comprise program instructions to perform coarse alignment 170 of the new image 120 and the reference image 130. Program instructions to perform coarse alignment 170 may comprise program instructions for estimating scale and rotation 171, performing convolution 172, and performing low-resolution alignment 173 of the new image 120 and the reference image 130 according to the methods of the present disclosure. Program instructions to perform low-resolution alignment 173 may comprise non-linear mapping 173 or warping and point matching 175 according to the methods described herein.

Program instructions to perform coarse alignment 170 may enable a coarse aligned new image 176 and a coarse aligned reference image 177. The image processing system 150 may comprise program instructions to perform high-resolution alignment 180 of the coarse aligned new image 176 and the coarse aligned reference image 177. Program instructions to perform high-resolution alignment 180 may comprise program instructions to perform non-linear mapping 174 and point matching 175 according to the methods of the present disclosure.

The system 100 may comprise program instructions for a user to select whether to perform non-linear mapping 174 on either the new image 120 and/or the reference image 130.

The image processing system 150 may comprise program instructions to perform cross-checking 190 of point matches. Program instructions to perform cross-checking 190 may comprise point matching 175, remove errors 191, and perform confirmation of point matches 192, generating a high-resolution reference image 210 and a high-resolution new image 200 according to the methods of the present disclosure.

Figure 4:
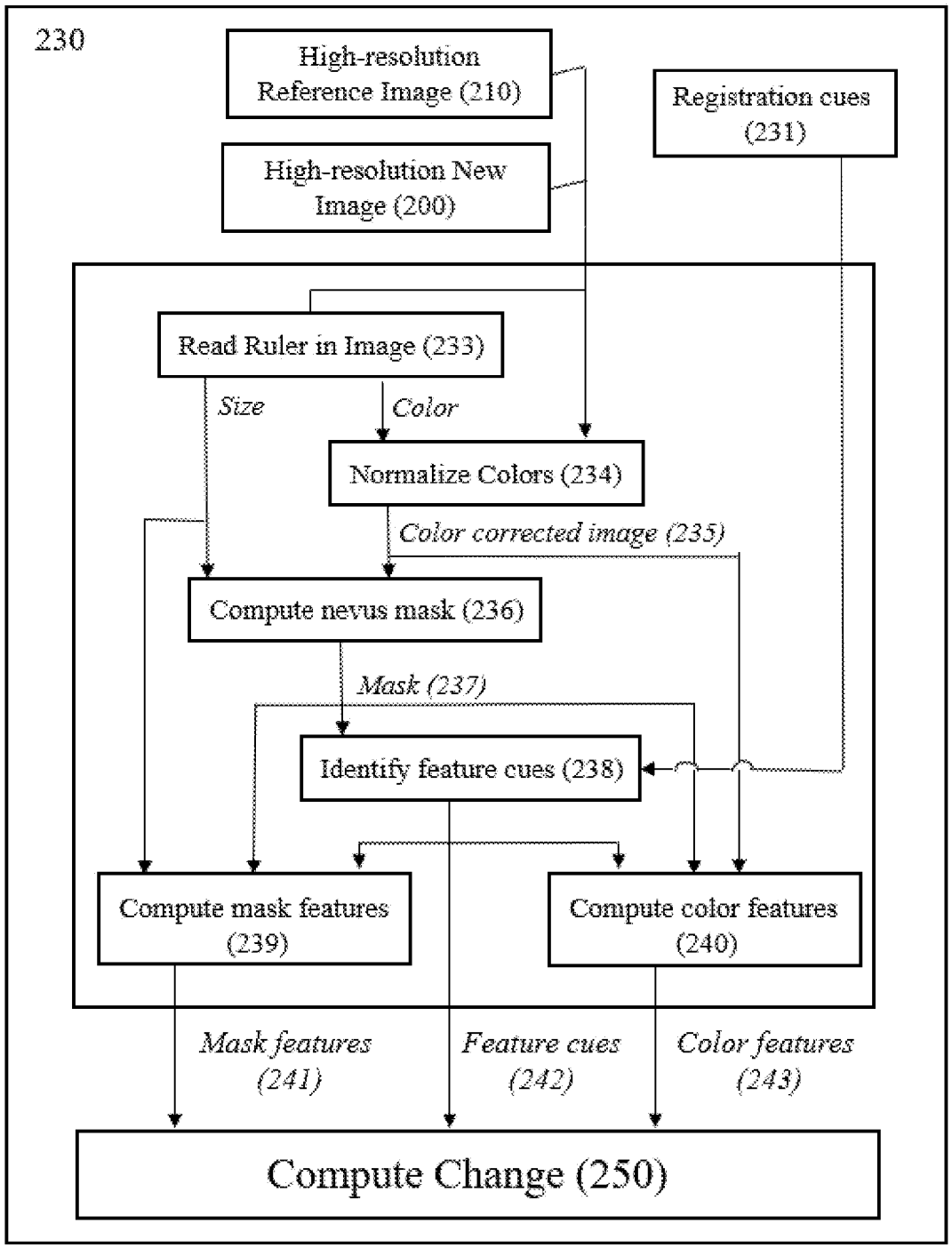
FIG. 4 is a schematic diagram of an image analysis system in accordance with certain aspects of the present disclosure.
Figure 5A:
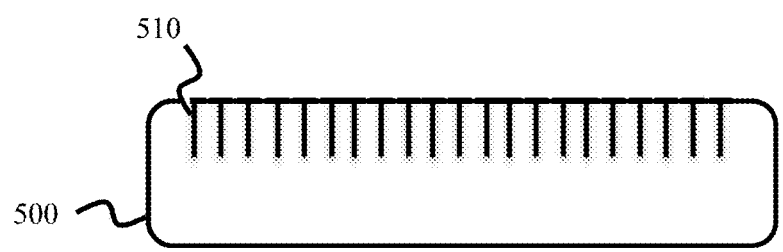
FIGS. 5A & 5B are illustrations of rulers that may be used by the image analysis system of the present disclosure.
Figure 5B:
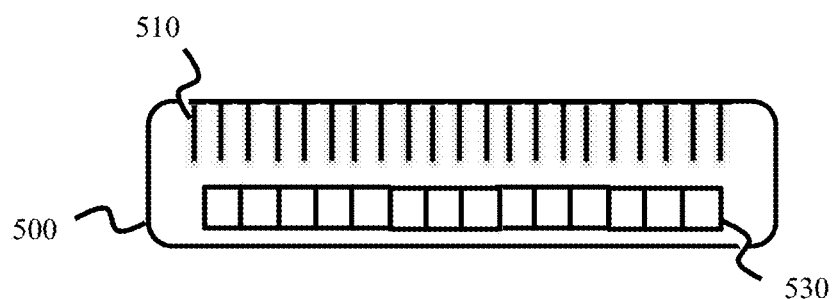

FIG. 4 depicts a block diagram of the image analysis system 230 according to certain aspects of the present disclosure. The image analysis system 230 may comprise program instructions to analyze at least one lesion of the high-resolution new image 200 and the high-resolution reference image 210. Performing analysis on at least one lesion may comprise calculating size features of a lesion, including, but not limited to, area, diameter, perimeter, and the like. Performing analysis may also comprise calculating color features of a lesion. The image analysis system 230 may comprise program instructions to individually analyze the high-resolution new image 200 and high-resolution reference image 210, including, but not limited to, program instructions to measure the lesions using a ruler 500 (FIGS. 5A & 5B) by reading the ruler in an image 233 according to the methods of the present disclosure, wherein the image may comprise the high-resolution new image 200 having a ruler and/or the high-resolution reference image 210 having a ruler. The image analysis system 230 may comprise program instructions to compute a binary nevus mask 236, identify feature cues 238 from registration cues 231, and compute mask features 239 to calculate mask features 241 and feature cues 242 according to the methods of the present disclosure to compute change 250 of a lesion over time, particularly a change in size. To analyze the color of a lesion in the high-resolution new image 200 and the high-resolution reference image 210, the image analysis system 230 may comprise program instructions to read the ruler 500 having color swatches 530 (FIG. 5B) in the image 233 according to the methods of the present disclosure, wherein the image may comprise the high-resolution new image 200 having a ruler with color swatches 530 and the high-resolution reference image 210 having a ruler with color swatches 530. In some aspects, the ruler 500 may comprise different color swatches 530 to standardize color across images of different dates and lighting conditions. The ruler 500 may comprise any device as described in the methods above. The image analysis system 230 may comprise program instructions to normalize colors 234 in the high-resolution new image 200 and the high-resolution reference image 210 to generate a color corrected image 235 for each image, wherein the color corrected image 235 may be used to compute color features 240 and generate color features 243 of at least one lesion in the high-resolution new image 200 and the high-resolution reference image 210 to compute change 250 according to the methods of the present disclosure. The color corrected image 235 may comprise a color corrected high-resolution new image and/or a color corrected high-resolution reference image.

Figure 6:
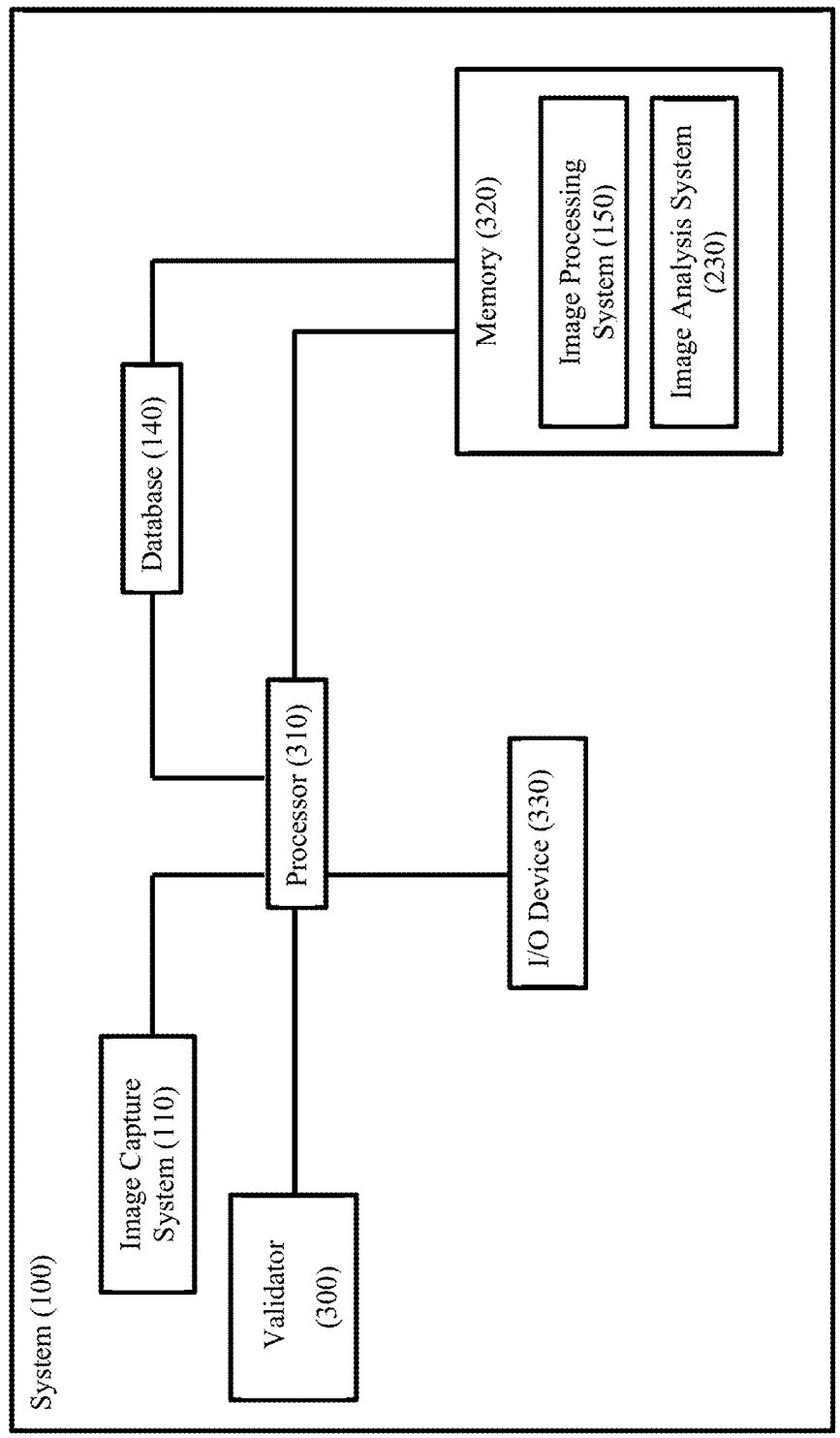
FIG. 6 is a block diagram of a system of the present disclosure.

FIG. 6 depicts a block diagram that schematically illustrates a system 100 according to the present disclosure. The system 100 may comprise a processor 310 that interfaces with memory 320 (which may be separate from or included as part of processor 310). The memory 320 may also employ cloud-based memory. In one aspect, the system may connect to a base station that includes memory and processing capabilities. The system may further comprise an I/O device 330. The processor 330 may interface with an image capture system 110 and database 140, wherein the image capture system 110 may obtain a new image according to the methods and systems of the present disclosure. The image capture system 110 may store the new image in the database 140, wherein the database may comprise at least one reference image.

Memory 320 has stored therein a number of routines that are executable by processor 310. The processor 310, in communication with the memory 320, may be configured to execute an image processing system 150. The image processing system 150 may comprise program instructions executable by processor 310 to align the new image and reference image according to the methods and systems of the present disclosure.

The processor 310, in communication with the memory 320, may be configured to execute an image analysis system 230. The image analysis system 230 may comprise program instructions executable by processor 310 to analyze the high-resolution new image and high-resolution reference image according to the methods and systems of the present disclosure. The results of the analysis of the images may be displayed on a validator 300 according to the systems and methods of the present disclosure.

Processor 310 may be one or more microprocessors, microcontroller, an application specific integrated circuit (ASIC), a circuit containing one or more processing components, a group of distributed processing components, circuitry for supporting a microprocessor, or other suitable processing device that interfaces with memory 320. Processor 310 is also configured to execute computer code stored in memory 320 to complete and facilitate the activities described herein.

I/O device 330 (including, but not limited to, keyboards, displays, pointing devices, DASD, tape, CDs, DVDs, thumb drives and other memory media, etc.) may be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards may be just a few of the available types of network adapters.

As will be appreciated by one skilled in the art, the present disclosure may be embodied as a system, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "system." Furthermore, the presently disclosed invention may take the form of a computer program product embodied in any tangible medium of expression having computer useable program code embodied in the medium.

Figure 7:
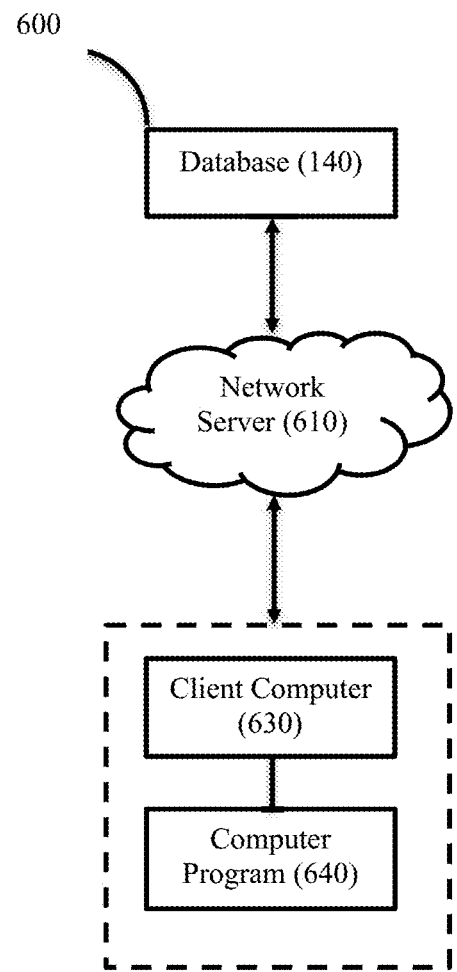
FIG. 7 is a schematic diagram of a computer network system for registering two or more patient images for change assessment over time according to the present disclosure.

FIG. 7 depicts a schematic diagram of a system of the present disclosure comprising a client computer 630 and a computer program 640 configured to execute the methods and systems of the present disclosure. The client computer 630 may be any device capable of executing the computer program 640 of the present disclosure. The system may interface with at least one network server 610, wherein the at least one network server 610 may interface with a database 140 and the system.

Although the depicted system is shown and described herein with certain components and functionality, other aspects of the system may be implemented with fewer or more components or with less or more functionality. Some aspects of the system may comprise a plurality of network servers 610, a plurality of networks, and a plurality of databases 140. Some aspects may include similar components arranged in another manner to provide similar functionality in one or more aspects.

The client computer 630 manages the interface between a system user and the computer program 640 and network server 610. Although the present disclosure is described with regard to a "computer", it should be noted that optionally any device featuring a data processor and the ability to execute one or more instructions may be described as a computer, including but not limited to any type of personal computer (PC), a server, a distributed server, a virtual server, a cloud computing platform, a cellular telephone, an IP telephone, a smartphone, a mobile device, or a personal digital assistant (PDA). Any two or more of such devices in communication with each other may optionally comprise a network or a computer network.

The network may communicate traditional block I/O, for example, over a storage area network (SAN). The network may also communicate file I/O, for example, using a transmission control protocol/internet protocol (TCP/IP) network or similar communication protocol. In one aspect, the storage system includes two or more networks. In another aspect, the client computer 630 is connected directly to a network server 610 via a backplane or system bus. In one aspect, the network server 610 includes a cellular network, other similar types of networks, or combinations thereof.

The computing system may include clients and servers. A client and server are generally remote from each other and typically interact through a communication network. The relationship of client and server arises by virtue of computer programs running on the respective computers and having a client-server relationship to each other. In some aspects, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

Any combination of one or more computer useable or computer readable medium(s) may be utilized. The computer-useable or computer-readable medium may be, for example but not limited to, an electronic, magnetic, optical, electromagnetic, infrared, or semiconductor system, apparatus, device, or propagation medium. Computer-readable medium may also be an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, a magnetic storage device, a digital versatile disk (DVD), a memory stick, a floppy disk, a mechanically encoded device such as punch-cards or raised structures in a groove having instructions recorded thereon, and any suitable combination of the foregoing. Note that the computer-useable or computer-readable medium may be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-useable or computer-readable medium may be any medium that can contain, store, communicate, propagate, or transport the program for use by or in connection with the instruction execution system, apparatus, or device. The computer-useable program code may be transmitted using any appropriate medium, including but not limited to wireless, wireline, optical fiber cable, RF, etc.

Computer program code for carrying out operations of the presently disclosed invention may be written in any combination of one or more programming languages. The programming language may be, but is not limited to, object-oriented programming languages (Java, Smalltalk, C++, etc.) or conventional procedural programming languages ("C" programming language, etc.). The program code may execute entirely on a user's computer, partly on the user's computer, as a stand-alone software package, partly on a user's computer and partly on a remote computer, or entirely on the remote computer or server. In the latter scenario, the remote computer may be connected to the user's computer through any type of network, including a local area network (LAN) or a wide area network (WAN), or the connection may be made to an external computer, which may include through the Internet using an Internet Services Provider. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

The systems and methods of the present disclosure may process data on any commercially available computer. In other aspects, a computer operating system may include, but is not limited to, Linux, Windows, UNIX, Android, MAC OS, and the like. In one aspect of the present disclosure, the forgoing processing devices or any other electronic, computation platform of a type designed for electronic processing of digital data as herein disclosed may be used.

Aspects of the present disclosure are described with reference to flowchart illustrations and/or block diagrams of methods, systems, and computer program products according to aspects of the present disclosure. It will be understood that each block of the flowchart illustrations and/or block diagrams, and combination of blocks in the flowchart illustrations and/or block diagrams, may be implemented by computer program instructions. These computer program instructions may be provided to a processor of a general-purpose computer, special purpose computer, or other programmable data processing apparatus to produce a machine, which the instructions execute via the processor of the computer or other programmable data processing apparatus allowing for the implementation of the steps specified in the flowchart and/or block diagram blocks or blocks.

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others.

Definitions

Unless otherwise defined, all terms (including technical and scientific terms) used herein have the same meaning as commonly understood by one of ordinary skill in the art to which this disclosure belongs. As such, terms, such as those defined by commonly used dictionaries, should be interpreted as having a meaning that is consistent with their meaning in a context of a relevant art and should not be interpreted in an idealized or overly formal sense unless expressly so defined herein.

As used herein, the term "lesion" refers to any mark different from the average pigmentation around it. As such a "lesion" may include, but is not limited to, a nevus, a pore, a birth mark, a freckle, a scar, and the like.

As used herein, the term "user" refers to any person, entity, corporation, individual, institution, medical provider, medical facility, physician, physician assistant, nurse, nurse practitioner, doctor, patient, and the like capable of utilizing the methods and systems of the present disclosure.

As used herein, the term "patient" refers to any animal or human capable of receiving medical assistance or diagnostics according to the methods and systems of the present disclosure.

As used herein, the term "and/or" includes any and all combinations of one or more of the associated listed items. Likewise, as used in the following detailed description, the term "or" is intended to mean an inclusive "or" rather than an exclusive "or." That is, unless specified otherwise, or clear from context, "X employs A or B" is intended to mean nay of the natural inclusive permutations. Thus, if X employs A; X employs B; or X employs both A and B, then "X employs A or B" is satisfied under any of the foregoing instances.

The terminology used herein is for the purpose of describing particular examples only and is not intended to be limiting. As used herein, the singular forms "a", "an", and "the" may be intended to include the plural forms as well, unless the context clearly dictates otherwise. As example, "a" lesion may comprise one or more lesions, and the like.

The terms "comprises", "comprising", "including", "having", and "characterized by", may be inclusive and therefore specify the presence of stated features, elements, compositions, steps, integers, operations, and/or components, but do not preclude the presence or addition of one or more other features, integers, steps, operations, elements, components, and/or groups thereof. Although these open-ended terms may be to be understood as a non-restrictive term used to describe and claim various aspects set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, described herein also specifically includes embodiments consisting of, or consisting essentially of, such recited compositions, materials, components, elements, features, integers, operations, and/or process steps. In the case of "consisting of", the alternative embodiment excludes any additional compositions, materials, components, elements, features, integers, operations, and/or process steps, while in the case of "consisting essentially of", any additional compositions, materials, components, elements, features, integers, operations, and/or process steps that materially affect the basic and novel characteristics may be excluded from such an embodiment, but any compositions, materials, components, elements, features, integers, operations, and/or process steps that do not materially affect the basic and novel characteristics may be included in the embodiment.

Any method steps, processes, and operations described herein may not be construed as necessarily requiring their performance in the particular order discussed or illustrated, unless specifically identified as an order of performance. It is also understood that additional or alternative steps may be employed, unless otherwise indicated.

In addition, features described with respect to certain example embodiments may be combined in or with various other example embodiments in any permutational or combinatory manner. Different aspects or elements of example embodiments, as disclosed herein, may be combined in a similar manner. The term "combination", "combinatory," or "combinations thereof" as used herein refers to all permutations and combinations of the listed items preceding the term. For example. "A, B, C, or combinations thereof" is intended to include at least one of: A, B, C, AB, AC. BC, or ABC, and if order is important in a particular context, also BA, CA, CB, CBA, BCA, ACB, BAC, or CAB. Continuing with this example, expressly included may be combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

Aspects of the present disclosure may be described herein with reference to flowchart illustrations and/or block diagrams of methods, apparatus (systems), and computer program products according to aspects of the disclosure. It will be understood that each block of the flowchart illustrations and/or block diagrams, and combinations of blocks in the flowchart illustrations and/or block diagrams, may be implemented by computer readable program instructions. The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and block diagrams in the Figures illustrate the architecture, functionality, and operation of possible implementations of systems, methods, and computer program products according to various aspects of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

Words such as "then," "next," etc. are not intended to limit the order of the steps; these words may be simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

In the description, certain details are set forth in order to provide a better understanding of various embodiments of the systems and methods disclosed herein. However, one skilled in the art will understand that these embodiments may be practiced without these details and/or in the absence of any details not described herein. In other instances, well-known structures, methods, and/or techniques associated with methods of practicing the various embodiments may not be shown or described in detail to avoid unnecessarily obscuring descriptions of other details of the various embodiments.

While specific aspects of the disclosure have been provided hereinabove, the disclosure may, however, be embodied in many different forms and should not be construed as necessarily being limited to only the embodiments disclosed herein. Rather, these embodiments may be provided so that this disclosure is thorough and complete, and fully conveys various concepts of this disclosure to skilled artisans.

Furthermore, when this disclosure states that something is "based on" something else, then such statement refers to a basis which may be based on one or more other things as well. In other words, unless expressly indicated otherwise, as used herein "based on" inclusively means "based at least in part on" or "based at least partially on."

All numerical quantities stated herein may be approximate, unless stated otherwise. Accordingly, the term "about" may be inferred when not expressly stated. The numerical quantities disclosed herein may be to be understood as not being strictly limited to the exact numerical values recited. Instead, unless stated otherwise, each numerical value stated herein is intended to mean both the recited value and a functionally equivalent range surrounding that value. At the very least, and not as an attempt to limit the application of the doctrine of equivalents to the scope of the claims, each numerical value should at least be construed in light of the number of reported significant digits and by applying ordinary rounding processes. Typical exemplary degrees of error may be within 20%, 10%, or 5% of a given value or range of values. Alternatively, the term "about" refers to values within an order of magnitude, potentially within 5-fold or 2-fold of a given value. Notwithstanding the approximations of numerical quantities stated herein, the numerical quantities described in specific examples of actual measured values may be reported as precisely as possible. Any numerical values, however, inherently contain certain errors necessarily resulting from the standard deviation found in their respective testing measurements.

All numerical ranges stated herein include all sub-ranges subsumed therein. For example, a range of "1 to 10" or "1-10" is intended to include all sub-ranges between and including the recited minimum value of 1 and the recited maximum value of 10 because the disclosed numerical ranges may be continuous and include every value between the minimum and maximum values. Any maximum numerical limitation recited herein is intended to include all lower numerical limitations. Any minimum numerical limitation recited herein is intended to include all higher numerical limitations.

Features or functionality described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, may be at least partially performed via at least one entity or actor in any manner.

All documents cited herein may be incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to this application.

While particular embodiments have been illustrated and described, it would be obvious to those skilled in the art that various other changes and modifications may be made without departing from the spirit and scope of the invention. Those skilled in the art will recognize or be able to ascertain using no more than routine experimentation, numerous equivalents to the specific apparatuses and methods described herein, including alternatives, variants, additions, deletions, modifications, and substitutions. This application including the appended claims is therefore intended to cover all such changes and modifications that may be within the scope of this application.

Aspects

Aspect 1: A method of registering two or more patients images for change assessment over time, comprising: obtaining a new image of an area with an image capture system; obtaining a reference image of a similar area; performing pre-processing of the new image and the reference image, wherein at least one point is determined in the new image that corresponds to at least one point in the reference image, and wherein a point is a centroid of at least one lesion; performing a coarse alignment of the new image and the reference image to coarse align the at least one point in the reference image and the at least one point in the new image to generate a point match; performing a high-resolution estimate to generate a high-resolution new image and a high-resolution reference image, wherein the high-resolution new image and the high-resolution reference image have an increased number of points; performing an alignment of the high-resolution new image and the high-resolution reference image, wherein the high-resolution new image and the high-resolution reference image have an increased number of point matches; cross-checking the at least one-point match to eliminate false matches and confirm correct matches of the high-resolution new image and the high-resolution reference image; performing segmentation of the high-resolution new image and the high-resolution reference image to distinguish at least one lesion from the area; performing analysis on the at least one lesion in the high-resolution new image and the high-resolution reference image; and displaying a result of the analysis on a validator.

Aspect 2: The method of aspect 1, wherein the method is invariant to differences in translation, rotation, warping, and lighting of the new image and the reference image.

Aspect 3: The method according to any of the foregoing aspects, further comprising: flickering the high-resolution new image and the high-resolution reference image back and forth.

Aspect 4: The method according to any of the foregoing aspects, wherein the area comprises skin of a patient.

Aspect 5: The method according to any of the foregoing aspects, wherein the at least one lesion is a nevus.

Aspect 6: The method according to any of the foregoing aspects, wherein performing analysis on at least one lesion comprises: calculating a change or percent change of a nevus, wherein change is a difference between a feature value of the reference image and a same feature value of the new image.

Aspect 7: The method according to any of the foregoing aspects, wherein the image capture system comprises a camera.

Aspect 8: The method according to any of the foregoing aspects, wherein the area of the reference image comprises at least 40% overlap of the area of the new image.

Aspect 9: The method according to any of the foregoing aspects, wherein pre-processing comprises segmentation of the new image and the reference image.

Aspect 10: The method according to any of the foregoing aspects, wherein performing segmentation of the new image and the reference image comprises: converting a red-green-blue image into at least three separate images for hue, saturation, and intensity, respectively; recombining the at least three separate images to create a unified segmentation; and determining the boundary between the at least one feature and the area.

Aspect 11: The method according to any of the foregoing aspects, wherein performing a coarse alignment of the new image and the reference image comprises performing a low-resolution translation, wherein a low-resolution translation comprises: performing point matching and performing non-linear mapping.

Aspect 12: The method according to any of the foregoing aspects, wherein performing a high-resolution translation estimate further comprises performing point matching and performing non-linear mapping.

Aspect 13: The method according to any of the foregoing aspects, wherein the coarse alignment, the high-resolution alignment, and cross-checking are performed at least a second time until all point matches are correctly matched.

Aspect 14: The method according to any of the foregoing aspects, wherein performing analysis on at least one lesions comprises: calculating a feature of a lesion, wherein a feature is selected from: area, diameter, perimeter, asymmetry, border irregularity, color, and evolution.

Aspect 15: The method according to any of the foregoing aspects, wherein displaying a result on a graphical user interface comprises: generating a report to a medical provider.

Aspect 16: The method according to any of the foregoing aspects, wherein the method is used for skin cancer screening of at least one nevus.

Aspect 17: A system for registering two or more images for change assessment over time, comprising: an image capture system configured to obtain a new image; a database having at least one reference image; a processor; and a memory storing computer-readable instructions that, when executed by the processor, cause the processor to trigger execution of an image processing system, wherein the image processing system comprises program instructions to: perform pre-processing of the new image and the reference image, wherein at least one point is determined in the new image and the reference image, and wherein a point is a centroid of at least one lesion; perform a coarse alignment of the new image and the reference image to coarse align at least one point in the reference image and at least one point in the new image; perform a high-resolution estimate to generate a high-resolution new image and a high-resolution reference image, wherein the high-resolution new image and the high-resolution reference image have an increased number of points; perform an alignment of the high-resolution new image and the high-resolution reference image, wherein the high-resolution new image and the high-resolution reference image have an increased number of point matches; and cross-check the at least one-point match to eliminate false matches and confirm correct matches of the high-resolution new image and the high-resolution reference image; wherein the memory storing computer-readable instructions that, when executed by the processor, cause the processor to trigger execution of an image analysis system, wherein the image analysis system comprises program instructions to: perform segmentation of the high-resolution new image and the high-resolution reference image to distinguish at least one lesion from the area; perform analysis on at least one lesion in the high-resolution new image and the high-resolution reference image; and display a result on a validator.

Aspect 18: The system of aspect 17, further comprising: program instructions to flicker the high-resolution new image and the high-resolution reference image back and forth.

Aspect 19: The system according to any of the foregoing aspects, wherein the lesion is a nevus.

Aspect 20: The system according to any of the foregoing aspects, wherein program instructions to perform analysis on at least one lesion comprises: calculate a change or percent change of a nevus, wherein change is a difference between a feature value of the reference image and a same feature value of the new image.

Aspect 21: A computer program product for registering two or more patient images for change assessment over time, comprising at least one non-transitory computer readable medium including program instruction that, when executed by at least one processor, cause said at least one processor to: perform pre-processing of the new image and the reference image, wherein at least one point is determined in the new image and the reference image, and wherein a point is a centroid of at least one lesion; perform a coarse alignment of the new image and the reference image to coarse align at least one point in the reference image and at least one point in the new image; perform a high-resolution estimate to generate a high-resolution new image and a high-resolution reference image, wherein the high-resolution new image and the high-resolution reference image have an increased number of points; perform an alignment of the high-resolution new image and the high-resolution reference image, wherein the high-resolution new image and the high-resolution reference image have an increased number of point matches; cross-check the at least one-point match to eliminate false matches and confirm correct matches of the high-resolution new image and the high-resolution reference image; perform segmentation of the high-resolution new image and the high-resolution reference image to distinguish at least one lesion from the area; perform analysis on at least one lesion in the high-resolution new image and the high-resolution reference image; and display a result on a validator.

EXAMPLES

Example 1

The systems and methods of the present disclosure generated automated image registration to facilitate the detection and quantification of changes in size and number of pigmented lesions of interest in sequential digital images by melanoma clinicians.

Image pairs of the posterior trunk from 24 patients were obtained from an archival image database, of which seven were excluded from analysis. The most common reasons for exclusion were image pairs with too few features to register; images with poor acquisition, such as uneven/poor cropping; and durations greater than 6 years between images.

Of the patients whose images were analyzed, the mean age at the time of the first image was 38.4 years (range=8.8-79.0 years; SD=16.8 years). Seven patients were men, and 10 were women. Recorded Fitzpatrick skin types were Fitzpatrick 1 (four patients), Fitzpatrick 1-2 (two patients), Fitzpatrick 2 (eight patients), Fitzpatrick 2-3 (one patient), and unknown (two patients). Among patients for whom historical information was available, 14 carried a previous diagnosis of melanoma. The remaining three patients did not have a previous histopathologic diagnosis available. One patient had two pairs of images, so there were 18 total image pairs included in the analysis. The mean time between pair images was 3.4 years (range—0.5-7.2 years; SD=1.4 years).

To assess whether registration and alignment by the systems and methods of the present disclosure improved a clinician's ability to detect a change, three practicing dermatologists and two medical oncologists involved in the care of patients with melanoma reviewed the paired serial full-back images and enumerated the number of pigmented lesion pairs in several categories: decreased, disappeared, surgically removed, increased, or appeared.

Figure 8A:
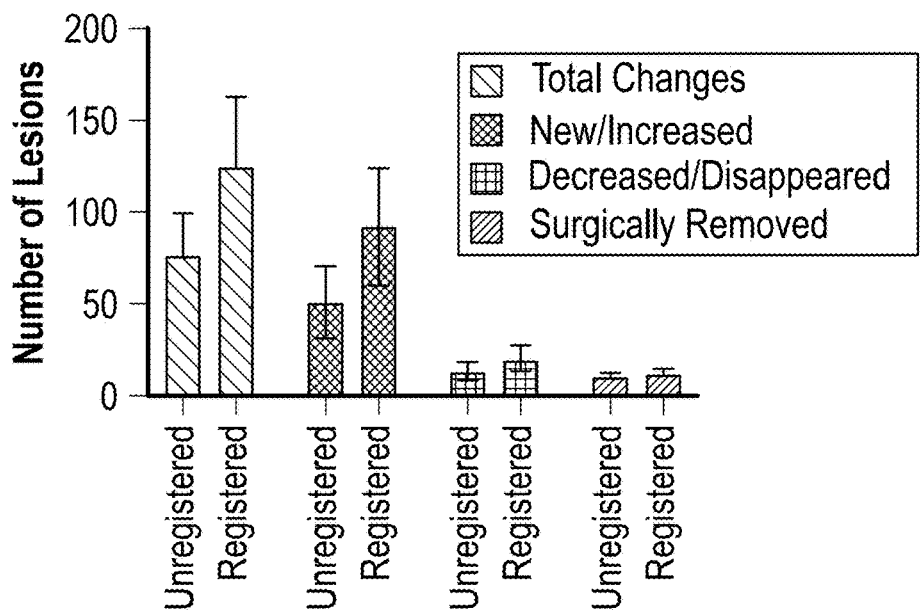
FIG. 8A is a graph of lesion change by category (total changes, new/increased, decreased/disappeared, and surgically removed).
Figure 8B:
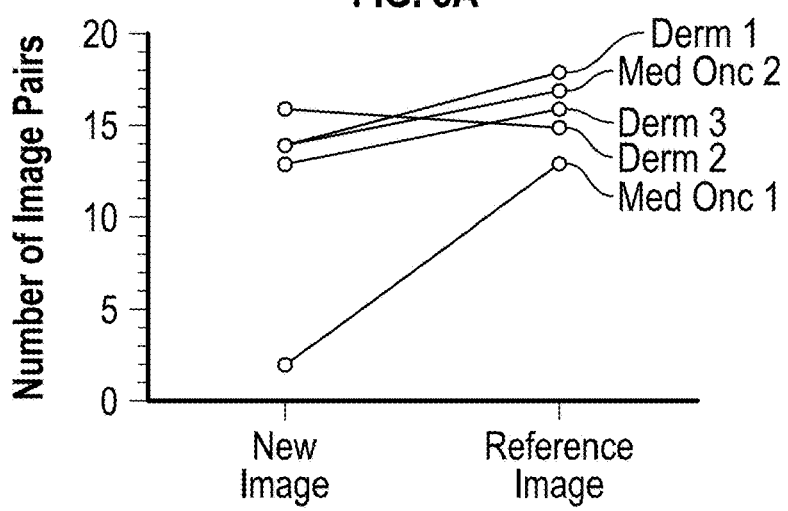
FIG. 8B is a graph of the number of image pairs with new/increased lesions detected.
Figure 8C:
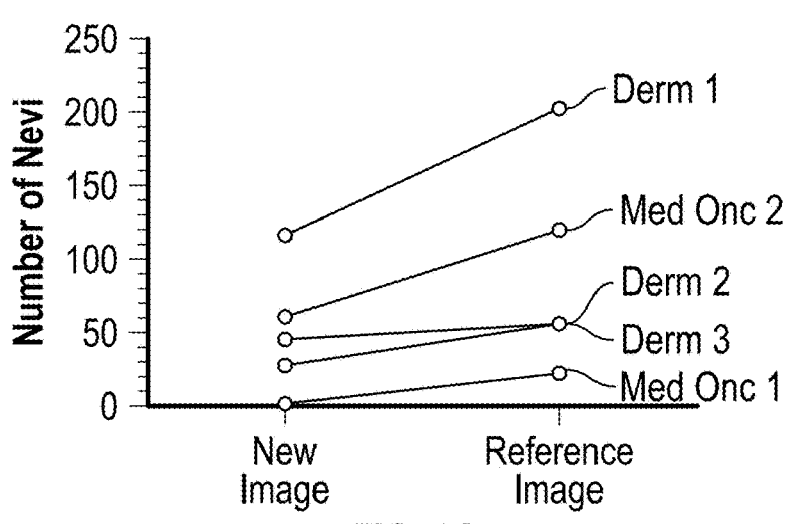
FIG. 8C is a graph of the number of image pairs with new/increasing lesions detected.

To reduce the potential for bias due to carry-over effect, the images in each set (registered and unregistered) were presented in random order, and each set of images was presented during different viewing sessions, with the unregistered images shown first. The mean delay between viewing the first and second sets of images was 14 days (range=0.167-40 days; SD=17 days). Clinician use of the systems and methods of the present disclosure increased the number of lesions detected in several categories; total changed lesions, new/increased lesions, decreased/disappeared lesions, surgically removed lesions (FIG. 8A), and image pairs with new/increased lesions detected (FIG. 8B). The increase in the detection of total changed lesions (average=1.7-fold increase) was primarily driven by a 1.8-fold average increase in detection of new or increased lesions. The changes in decreased/disappearing lesions and surgically removed lesions were less consistent and of lower magnitude.

The methods and systems of the present disclosure improved the detection of new or increased lesions by all providers (FIG. 8A), despite differences in the specialty of the provider, the amount of time elapsed between viewing the unregistered and registered images, and the baseline number of images detected in each category. Complete numerical results are provided in FIG. 14.

The systems and methods of the present disclosure produced statistically significant improvements in the identification of new and increased lesions (P<0.001) and in the identification of image pairs with changes detected (P<0.001) versus unregistered images, as assessed by linear mixed effects models. The ORs for changes detected between registered and unregistered images was 4.85 (95% confidence interval [CI]=2.06-11.39).

To evaluate the accuracy of the systems and methods of the present disclosure to identify nevi and other cutaneous lesions, we compared the results of lesion identification by the systems and methods with those of clinician review of 46 randomly selected subfields of the posterior truncal images by two medical oncologists and one advanced practice provider, all of whom were involved in the care of patients with melanoma. A consensus of three of the three clinicians was considered a gold standard of lesion identification. Of note, there were no disagreements between clinicians regarding nevus identification.

For lesions over 2 mm where three of the three clinicians identified a nevus, the systems and methods agreed for 67 of 69 lesions. This corresponds to a false negative rate of 2.90% (exact 95% CI=0.8-7.5%) and a sensitivity of 97.1% (exact 95% CI=92.5%-9.2%). The two nevi the systems and methods did not agree for were small nevi that were counted together with immediately adjacent larger nevi.

Non-nevus lesions detected by the systems and methods were classified by clinicians as seborrheic keratoses, but other nonmelanocytic structures were identified as well, including, occasional suspected artifacts including possible dust on the camera lens.

Two methods were used to assess whether the systems and methods of the present disclosure had successfully registered nevi between time points for individual patients. The first method involved a change detection exercise involving aligned posterior truncal images displayed as sequential PowerPoint slides. The five clinician reviewers who participated in this exercise determined that on average, 17 of 18 images (range ¼ 15-18) had greater than 90% of lesions correctly aligned. The second method involved comparison in the Validator application of 97 paired fields, which included a variety of lesion types, including those with increasing, decreasing, appearing, and disappearing lesions. Of the 97 paired fields, 87 clearly had lesions identified in both images, whereas the remaining 10 had lesions identified that either appeared or disappeared. The three clinician reviewers who completed this exercise determined that all 87 images included in this analysis that had paired lesions in the subsequent image had been correctly registered. Of note, lesions on the edges of the images had been specifically excluded from this analysis.

To compare the assessment of size change by humans with the quantification of the systems and methods of the present disclosure, three clinicians (two medical oncologists and one advanced practice provider) were shown sequential zoomed-in views of lesion pairs in the Validator interface. Clinicians were asked to characterize changes in the size of the lesions on an ordinal scale. Interrater reliability between a clinician and the other and between each clinician and the systems and methods of the present disclosure was computed using Cohen's kappa. Data are presented as weighted kappas. Quadratic weighting gave harsher penalties to larger disagreements, and it produced results similar to those of Fleiss intraclass correlation. We reported both linear and quadratic weights (FIG. 9).

Figure 9:
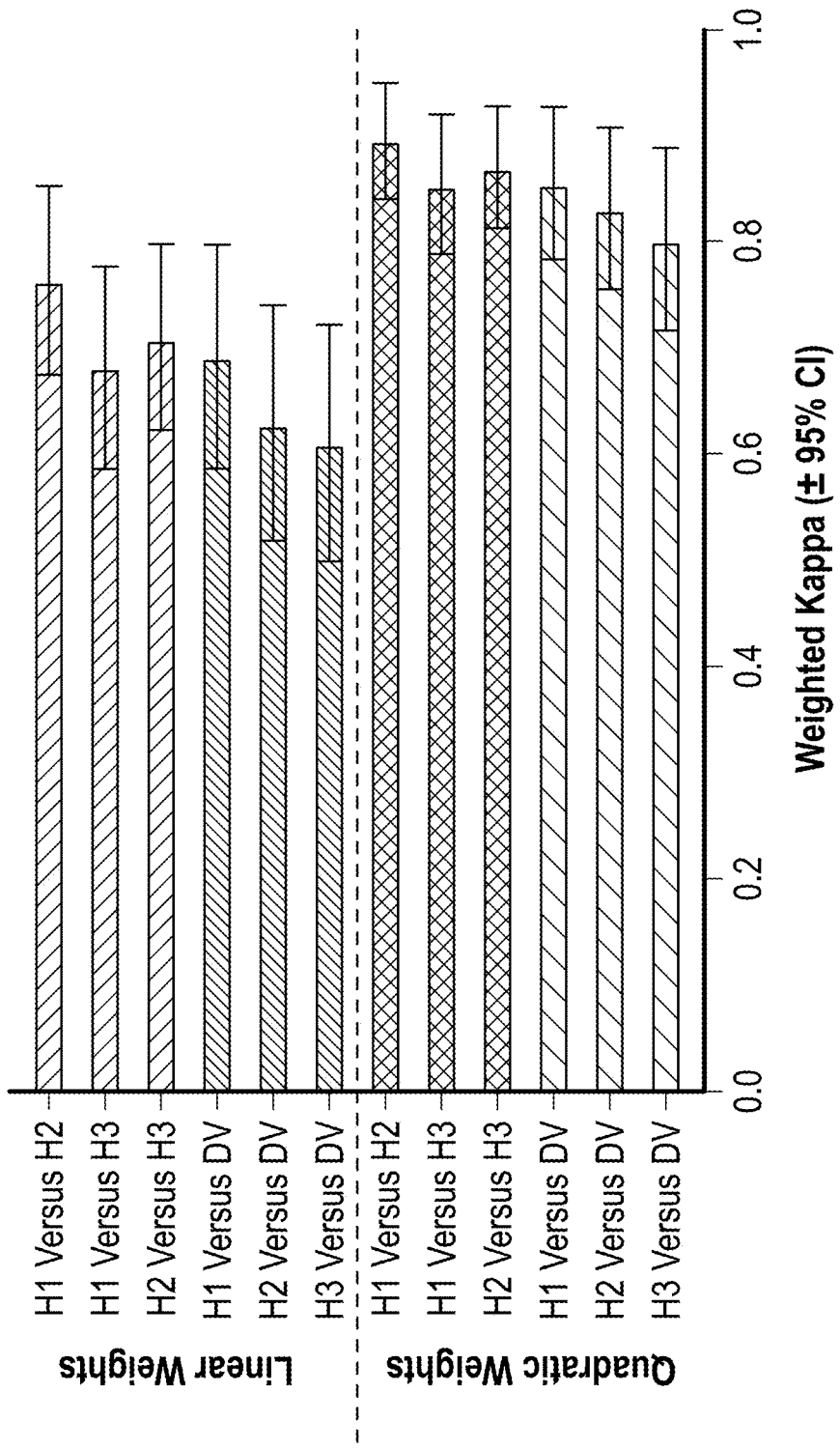
FIG. 9 is a graph of size change assessment by the methods and systems of the present disclosure compared with human observers (H1, H2, H3) and between each human observer and the methods and systems of the present disclosure.

As shown in FIG. 9, clinicians demonstrated moderate (with linear weights) to good (with quadratic weights) agreement with each other. The methods and systems of the present disclosure showed moderate (with linear weights) to good (with quadratic weights) agreement with the clinicians. The weighted kappas were slightly lower for the systems and methods of the present disclosure than for the human raters; however, the 95% CIs overlapped such that the difference was not significant for any rater pair.

Overall, the systems and methods of the present disclosure identified numerous changes in lesions that were missed in the original unregistered images. Because the systems and methods of the present disclosure use images of large areas of skin, it offers benefits over conventional clinical practice of change assessment such as dermoscopy of a single lesion. The systems and methods of the present disclosure tracked multiple pigmented lesions contained in the images and computed an accurate relative change between sequential image dates.

The validator (FIGS. 11 through 13) of the present disclosure allowed clinicians to assess features of the systems and methods of the present disclosure and classify and characterize lesions detected by the systems and methods of the present disclosure. It allowed specific prompts and responses to be modified.

Materials and Methods: Serial posterior truncal photographs from patients with multiple atypical nevi and a history of melanoma were obtained from a pre-existing image and nevus biobanking protocol database at UPMC Hillman Cancer Center (Pittsburgh, PA). The original images were taken under protocol UPCI 96-099 (institutional review board number REN18100233/IRB970186 approved by the University of Pittsburgh Institutional Review Board) using a single Nikon D700 camera and a standardized background and automatic focus and exposure settings. They were stored using Philips' iSITE PACS (Philips, Amsterdam, The Netherlands). Patients provided written informed consent for the use of the deidentified images in future research. The images were stripped of all identifiers other than a study-specific identification code. Preprocessing consisted only of cropping some images to remove the arms; the images were then analyzed using the systems and methods of the present disclosure.

For inclusion in the study, the patients' images had to meet the following criteria: (i) the number of nevi/lesions imaged in the images was adequate for registration (roughly greater than 20), (ii) moderate posture changes (not severe), (iii) similar cropping (i.e., including/excluding shoulders), and (iv) an interval between imaging dates <6 years.

For the mobile photographs included in the study, images were acquired using an iphone 11 (Apple, Cupertino, CA). Neither the recruitment of the volunteer nor the photography was connected with clinical care; however, the processed images were provided to the patient to share with their healthcare providers.

For change assessment in the posterior truncal images, Clinicians were asked to review paired serial posterior truncal images presented as Microsoft PowerPoint slides that could be toggled back and forth between dates. The clinicians first reviewed the set of unmodified photographs and then, in a separate session, reviewed the same images that had been registered and aligned by the systems and methods of the present disclosure. There was no size threshold for lesions to be included.

Figure 11:
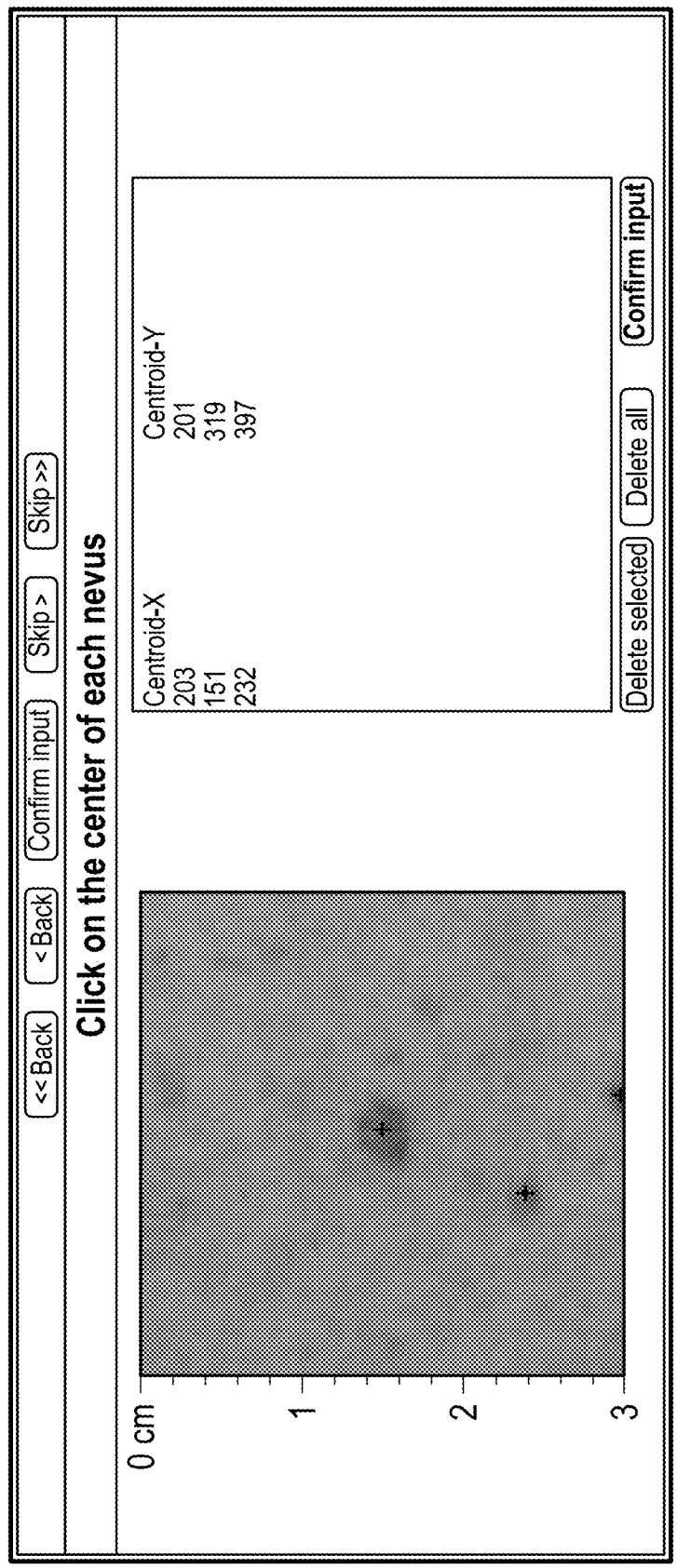
FIG. 11 is a screenshot view of a validator with lesion identification according to an aspect of the present disclosure.

For assessment of sensitivity, Clinicians were shown randomly chosen subfields of the posterior truncal images in the Validator application and asked to click on all pigmented lesions of interest in the images, which marked them with crosshairs and recorded the corresponding coordinates (FIG. 11). The systems and methods of the present disclosure then determined whether the crosshairs were within the segmentation boundaries of a lesion that had been identified by the systems and methods of the present disclosure. This allowed the identification of true positives (defined as lesions for which both clinicians and the systems and methods of the present disclosure identified a nevus), false negatives (defined as lesions for which clinicians but not the systems and methods of the present disclosure identified a distinct nevus), and non-nevus lesions (defined as lesions identified by the systems and methods of the present disclosure that were not identified as nevi by clinicians). Sensitivity was calculated as (true positives)/(true positives±false negatives).

For the first method of assessing the quality of registration, reviewers who completed the change assessment in posterior truncal images exercise with aligned PowerPoint slides were asked to comment on whether each image pair had approximately >90% of the lesions accurately registered as well as to comment subjectively on any issues with registration.

For the second method of assessing the quality of registration, a subset of lesions identified by the system and methods of the present disclosure was selected for clinician review on the basis of the following criteria: (i) all lesions over 4 mm in diameter; (ii) lesions with visibly apparent changes in paired images; and (iii) the largest remaining lesion in each quadrant of the posterior truncal image pair if lesions are present, excluding nevi near the edge of the images.

Clinicians were shown image pairs of randomly chosen lesions photographed on different dates in the validator and asked whether the serial image pairs were registered (FIG. 12). Registered was defined in the following way: if there is a change, at least 90% of the area of the smaller of the nevus pair is contained within the larger of the lesion pair. If there is no change, then the lesion pairs overlap by at least 90%. When the lesion pair is not correctly registered, the earlier and later date lesion do not align, that is, there is <90% overlap of the smaller lesion with the larger lesion. Two visualization options were offered: a view with the two time points shown side by side and a toggle view where the aligned mages could be toggled back and forth between time points. This section of the validator also allowed clinicians to classify the lesions by type from a drop-down menu.

The first method of assessing the accuracy of size change used the validator, for which a subset of lesions was selected for further analysis according to the three criteria specified in the previous section. Clinicians were shown sequential zoomed-in views of isolated lesions, which were chosen at random (FIG. 13). Two visualization options were offered: a view with the two time points shown side by side and a toggle view where the overlaid images could be toggled back and forth between time points. Clinicians were asked to approximately categorize the change observed into specific bins: disappeared (100%), substantial decrease (>30%), moderate decrease (15-30%), no/minimal change (<15%), moderate increase (15-30%), and a substantial increase (>30%). The results were compared between observers and with the systems and methods of the present disclosure's quantitative assessments of diameter and area.

For the number of new/increased lesions, a linear mixed model was used to study its association with image registration. For the variable detected, which is defined as 1 if a patient had new/increased lesions detected and as 0 otherwise, a linear mixed-effect logistic regression model was used to study its association with image registration. In both of the two mixed models above, the registration (=1 for a registered image, =0 for an unregistered image) was a fixed effect, and patient and clinician were two random effects. The first model was analyzed with Proc Mixed in SAS software (SAS Institute, Cary, NC). The second model was analyzed with SAS Proc GLIMMIX.

For the calculation of CIs for sensitivity and the false negative rate, we used the Clopper-Pearson interval, which is based on the cumulative probability of the binomial distribution.

For assessment of size change, Cohen's kappa was used to compute kappa values between each individual rater (humans 1-3 and the systems and methods of the present disclosure) using both linear and quadratic weights as well as 95% CIs for each comparison. Analysis was performed in Strata (StataCorp, College Station, TX) using the kappaetc program written by Daniel Klein and available through the Boston College Statistical Software Components archive.

What is claimed is:

1. A method of registering two or more patient images for change assessment over time, comprising:
    obtaining a new image of an area with an image capture system;
    obtaining a reference image of a similar area;
    performing pre-processing of the new image and the reference image, wherein at least one point is determined in the new image that corresponds to at least one point in the reference image, and wherein the at least one point comprises a centroid of a skin lesion;
    performing a coarse alignment of the new image and the reference image to coarse align the at least one point in the reference image and the at least one point in the new image to generate a point match of the new image and the reference image;
    performing a high-resolution estimate to generate a high-resolution new image and a high-resolution reference image, wherein the high-resolution new image and the high-resolution reference image have an increased number of points identified within the high-resolution new image and the high-resolution reference image in comparison with the new image and the reference image;
    performing an alignment of the high-resolution new image and the high-resolution reference image, wherein the high-resolution new image and the high-resolution reference image have an increased number of point matches in comparison with the coarse alignment;
    cross-checking the increased number of point matches to eliminate false matches and confirm correct matches of the high-resolution new image and the high-resolution reference image;
    performing segmentation of the high-resolution new image and the high-resolution reference image to distinguish at least one skin lesion from the area;
    performing analysis on the at least one skin lesion in the high-resolution new image and the high-resolution reference image; and
    displaying a result of the analysis on a validator.

2. The method of claim 1, wherein the method is invariant to differences in translation, rotation, warping, and lighting of the new image and the reference image.

3. The method of claim 1, further comprising: flickering the high-resolution new image and the high-resolution reference image back and forth.

4. The method of claim 1, wherein the area comprises skin of a patient.

5. The method of claim 4, wherein the at least one skin lesion is a nevus.

6. The method of claim 1, wherein performing analysis on at least one skin lesion comprises:
calculating a change or percent change of the at least one skin lesion, wherein the change is a difference between a feature value of the reference image and a same feature value of the new image.

7. The method of claim 1, wherein the image capture system comprises a camera.

8. The method of claim 1, wherein the area of the reference image comprises at least 40% overlap of the area of the new image.

9. The method of claim 1, wherein pre-processing comprises performing segmentation of the new image and the reference image.

10. The method of claim 9, wherein performing segmentation of the new image and the reference image comprises:
converting a red-green-blue image into at least three images, wherein the at least three images of red, green, and blue pixel value to determine hue, saturation, and intensity;
recombining the at least three images to create a unified segmentation; and
determining a boundary between the at least one feature and a background of the area.

11. The method of claim 1, wherein performing a coarse alignment of the new image and the reference image comprises performing a low-resolution translation, wherein the low-resolution translation comprises: performing point matching and performing non-linear mapping.

12. The method of claim 1, wherein performing the high-resolution estimate further comprises performing point matching and performing non-linear mapping to implement translation, rotation, and scaling.

13. The method of claim 1, wherein the coarse alignment, the high-resolution alignment, and cross-checking are performed at least a second time until all point matches are correctly matched.

14. The method of claim 1, wherein performing analysis on the at least one skin lesion comprises: calculating a feature of the at least one skin lesion, wherein a feature is selected from: area, diameter, perimeter, asymmetry, border irregularity, color, and evolution.

15. The method of claim 1, wherein displaying a result on a graphical user interface comprises: generating a report to a medical provider.

16. The method of claim 1, wherein the method is used for skin cancer screening of at least one nevus.

17. A system for registering two or more images for change assessment over time, comprising:
a database having at least one reference image;
a processor; and
a memory storing computer-readable instructions that, when executed by the processor, cause the processor to trigger execution of an image processing system, wherein the image processing system comprises program instructions to:
perform pre-processing of a new image and the at least one reference image, wherein at least one point is determined in the new image and the at least one reference image, and wherein the at least one point comprises a centroid of at least one skin lesion;
perform a coarse alignment of the new image and the reference image to coarse align at least one point in the reference image and at least one point in the new image to generate a point match of the new image and the reference image;
perform a high-resolution estimate to generate a high-resolution new image and a high-resolution reference image, wherein the high-resolution new image and the high-resolution reference image have an increased number of points identified within the high-resolution new image and the high-resolution reference image in comparison with the new image and the reference image;
perform an alignment of the high-resolution new image and the high-resolution reference image, wherein the high-resolution new image and the high-resolution reference image have an increased number of point matches in comparison with the coarse alignment; and
cross-check the increased number of point matches at least one-point match to eliminate false matches and confirm correct matches of the high-resolution new image and the high-resolution reference image;
wherein the memory storing computer-readable instructions that, when executed by the processor, cause the processor to trigger execution of an image analysis system, wherein the image analysis system comprises program instructions to:
perform segmentation of the high-resolution new image and the high-resolution reference image to distinguish at least one skin lesion from the area;
perform analysis on at least one skin lesion in the high-resolution new image and the high-resolution reference image; and
display a result of the analysis on a validator.

18. The system of claim 17, further comprising: program instructions to flicker the high-resolution new image and the high-resolution reference image back and forth.

19. The system of claim 17, wherein the skin lesion is a nevus.

20. The system of claim 17, wherein program instructions to perform analysis on at least one skin lesion comprises:
calculate a change or percent change of a nevus, wherein change is a difference between a feature value of the reference image and a same feature value of the new image.

21. A computer program product for registering two or more patient images for change assessment over time, comprising at least one non-transitory computer readable medium including program instruction that, when executed by at least one processor, cause said at least one processor to:
perform pre-processing of a new image and a reference image, wherein at least one point is determined in the new image and the reference image, and wherein the at least one point comprises a centroid of at least one skin lesion;
perform a coarse alignment of the new image and the reference image to coarse align at least one point in the reference image and at least one point in the new image to generate a point match of the new image and the reference image;
perform a high-resolution estimate to generate a high-resolution new image and a high-resolution reference image, wherein the high-resolution new image and the high-resolution reference image have an increased number of points identified within the high-resolution new image and the high-resolution reference image;

perform an alignment of the high-resolution new image and the high-resolution reference image, wherein the high-resolution new image and the high-resolution reference image have an increased number of point matches in comparison with the coarse alignment;

cross-check the increased number of point matches to eliminate false matches and confirm correct matches of the high-resolution new image and the high-resolution reference image;

perform segmentation of the high-resolution new image and the high-resolution reference image to distinguish at least one skin lesion from the area;

perform analysis on at least one skin lesion in the high-resolution new image and the high-resolution reference image; and display a result of the analysis on a validator.

* * * * *